US005883392A

United States Patent [19]

Schuetz

[11] Patent Number: 5,883,392

[45] Date of Patent: Mar. 16, 1999

[54] APPARATUS COMPRISING INDUCTIVE AND/OR POWER TRANSFER AND/OR VOLTAGE MULTIPLICATION COMPONENTS

[75] Inventor: Marlin Niles Schuetz, Raleigh, N.C.

[73] Assignee: Raychem Corporation, Menlo Park, Calif.

[21] Appl. No.: 44,264

[22] Filed: Mar. 19, 1998

Related U.S. Application Data

[62] Division of Ser. No. 781,973, Dec. 21, 1996, Pat. No. 5,777,538, which is a division of Ser. No. 428,615, Apr. 25, 1995, Pat. No. 5,604,352.

[51] Int. Cl.$^{6}$ .............................. A61N 5/00; H01F 38/20

[52] U.S. Cl. ........................................ 250/482.3; 336/173

[58] Field of Search .................................... 336/172, 173, 336/182, 188, 220, 223, 228; 250/492.3; 363/59–61

[56] References Cited

U.S. PATENT DOCUMENTS

| | | | |
|---|---|---|---|
| 2,875,394 | 2/1959 | Cleland | 321/15 |
| 3,119,971 | 1/1964 | Cleland et al. | 331/62 |
| 3,634,645 | 1/1972 | Lempert et al. | 250/492.3 |
| 3,720,847 | 3/1973 | Massar | 327/370 |
| 3,851,287 | 11/1974 | Miller et al. | 336/84 R |
| 4,544,905 | 10/1985 | Best et al. | 336/136 |
| 4,690,499 | 9/1987 | Taylor et al. | 350/96.23 |
| 5,237,165 | 8/1993 | Tingley, III | 235/492 |
| 5,283,728 | 2/1994 | Hobart | 363/100 |
| 5,416,440 | 5/1995 | Lyons et al. | 250/492.3 |
| 5,530,255 | 6/1996 | Lyons et al. | 250/492.3 |

*Primary Examiner*—Matthew Nguyen
*Attorney, Agent, or Firm*—Herbert G. Burkard

[57] ABSTRACT

Apparatus for irradiating a substrate is compact, transportable, rugged, high powered, and highly efficient. It includes an improved high voltage inductor (1–230), an improved power transfer apparatus (230–294), an improved voltage multiplication apparatus (500–575), an improved auxiliary power supply (600–619) for the voltage multiplication apparatus, improved accessibility self-shielding (700), and improved methods for radiation processing of solid or liquid materials.

15 Claims, 25 Drawing Sheets

FIG. 4b
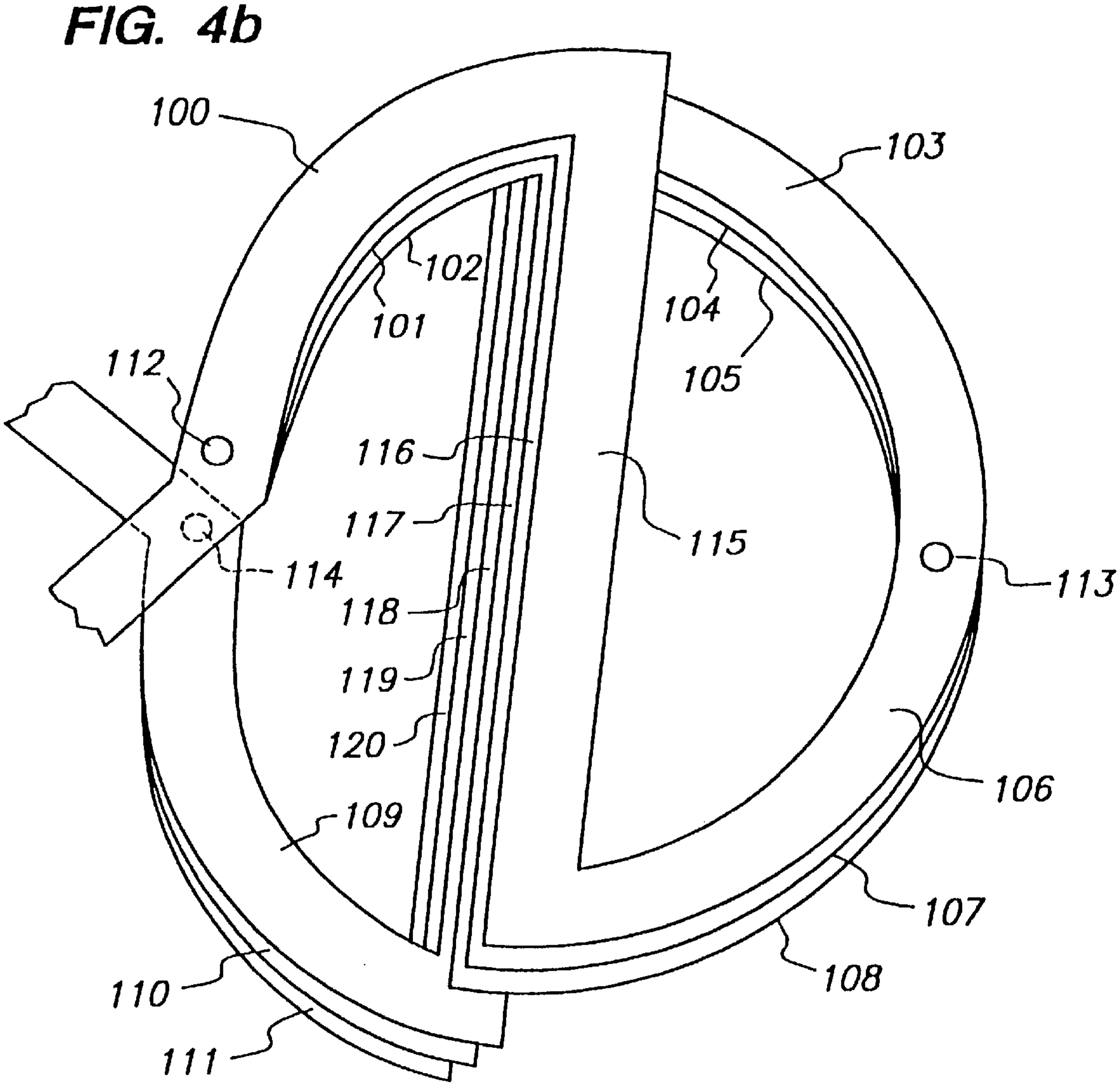
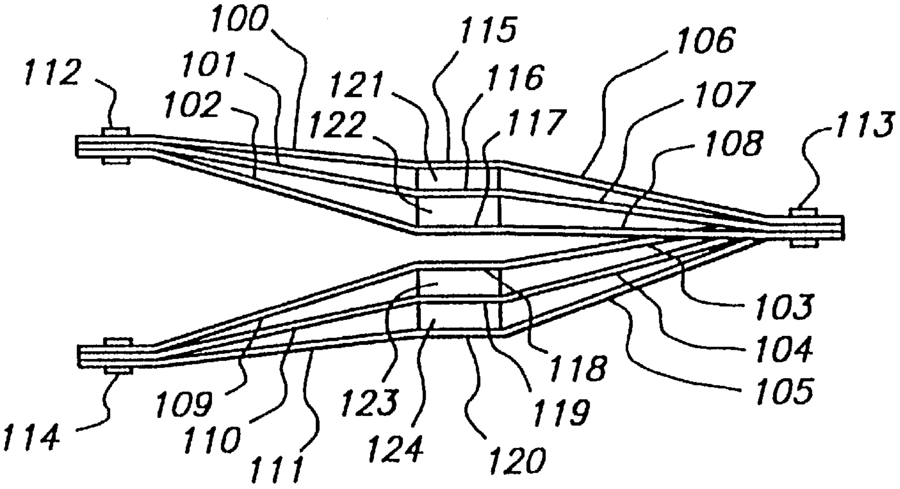
FIG. 4c

APPARATUS COMPRISING INDUCTIVE AND/OR POWER TRANSFER AND/OR VOLTAGE MULTIPLICATION COMPONENTS

REFERENCE TO RELATE APPLICATION

This application is a division of Ser. No. 08/781,973 filed on Dec. 21, 1996, now U.S. Pat. No. 5,777,538, which is a division of application Ser. No. 08/428,615, filed Apr. 25, 1995, now U.S. Pat. No. 5,604,352, the disclosures of which are hereby incorporated by reference in their entirety.

The present application is related to copending, U.S. patent application Ser. No. 07/950,530, filed on Sep. 23, 1992, which is a continuation-in-part of U.S. patent application Ser. No. 07/748,987, filed on Aug. 16, 1991, entitled “Transmission Window for Particle Accelerator”, now abandoned, which is a continuation-in-part of U.S. patent application Ser. No. 07/569,092 filed on Aug. 17, 1990, entitled “Transmission Window for Particle Accelerator”, now abandoned, and to copending U.S. patent application Ser. No. 08/198,163, filed on Feb. 17, 1994, entitled “Apparatus and Methods for Electron Beam radiation”, which is a continuation-in-part of copending Patent Cooperation Treaty Application No. US 93/08895 filed designating the U.S. on Sep. 22, 1993 and claiming priority from U.S. patent application Ser. No. 07/950,530, filed on Sep. 23, 1992, and also a continuation-in-part of copending U.S. patent application Ser. No. 07/950,530, filed on Sep. 23, 1992, which is a continuation-in-part of U.S. patent application Ser. No. 07/748,987, filed on Aug. 16, 1991, entitled “Transmission Window for Particle Accelerator”, now abandoned, which is a continuation-in-part of U.S. patent application Ser. No. 07/569,092 filed on Aug. 17, 1990, entitled “Transmission Window for Particle Accelerator”, now abandoned. The disclosures of all these applications are incorporated herein by reference for all purposes.

FIELD OF THE INVENTION

The present invention relates to improvements in high voltage power supplies especially suitable for use in apparatus for irradiating substrates, for example, high energy particle accelerators, such as may be used within industrial processes for treating various materials. More particularly, the present invention relates to improved power transfer apparatus of novel design comprising novel inductor components and improved voltage multiplication apparatus comprising novel capacitor assemblies, and to novel improved self-shielded apparatus for irradiating a substrate.

BACKGROUND OF THE INVENTION

Particle accelerators are employed to irradiate a wide variety of materials for several purposes. One purpose is to facilitate or aid molecular crosslinking or polymerization of plastic and/or resin materials. Other uses include sterilization of foodstuffs and medical supplies and sewage, and the destruction of toxic or polluting organic materials from water, sediments and soil.

A particle beam accelerator typically includes (i) an emitter for emitting the particle beam, (ii) an accelerator for energizing and shaping the emitted particles into a beam and for directing and accelerating the energized particle beam toward a target, (iii) usually a beam scanning or deflection means, and (iv) usually a transmission window and window mounting. A generator is provided for generating the considerable voltage difference needed to power the accelerator.

The generator frequently includes a power transfer apparatus, usually including a power oscillator, for supplying high voltage high frequency power to a remote load and voltage multiplication apparatus for converting the high frequency power into substantially constant high voltage DC output potential.

The emitter and the accelerator sections, which may comprise centrally arranged dynode elements or other beam shaping means, or electrostatic or electromagnetic lenses for shaping, focusing and directing the beam, are included within a high vacuum chamber so that air molecules do not interfere with the particle beam during the emitting, shaping, directing and accelerating processes.

The term “particle accelerator” includes accelerators for charged particles including, for example, electrons and heavier atomic particles, such as mesons or protons or other positive or negative ions. These particles may be charge neutralized subsequent to acceleration, usually prior to exiting the vacuum chamber.

The transmission window is provided at the target end of the vacuum chamber and enables the beam to pass therethrough to exit the vacuum chamber. The workpiece to be irradiated by the particle beam is usually positioned in the path of the particle beam, outside the accelerator vacuum chamber and adjacent the transmission window.

As used herein, the “transmission window” is a sheet of material which is substantially transparent to the particle beam. The transmission window is mounted on a window mounting comprising a support frame which includes securing and retention means which define a window envelope.

Conventionally, transmission windows are foils which have typically been installed between rectangular, generally flat flanges with filleted corners. The thin window foils are typically formed of titanium or titanium alloy sheets which typically range in thickness between about 0.0005 inches (0.013 mm) and 0.004 inches (0.104 mm). Much thicker stainless steel foils have been employed as transmission windows in irradiation apparatus for waste water/effluent processing.

Beams of this sort have many desireable uses. The efficacy of radiation-thermal cracking (RTC) and viscosity reduction of light and heavy petroleum stock, for example, has been reported in the prior art. Also, high energy particle experiments have been conducted in connection with processing of aqueous material including potable water, effluents, and waste products in order to reduce chemically or eliminate toxic organic materials, such as PCBs, dioxins, phenols, benzenes, trichloroetliylene, terrachloroethylene, aromatic compounds, etc.

Because of the known utility of particle radiation in the aforementioned processes, a need has arisen for a compact, transportable, rugged, high power, high efficiency particle accelerator apparatus. Cleland (U.S. Pat. No. 3,113,256) has suggested the use of an assembly of inductors in the shape of a toroid in an apparatus for generating high voltage high frequency (20–300 kHz) power to avoid “losses due to eddy currents”, which “are prohibitively high if the usual solenoidal type inductors are used”. To avoid strong radio frequency (RF) fields between opposite polarity terminals of neighboring inductors of the toroid, Cleland suggests reversing the direction of current flow and the winding sense in these adjacent inductors. Cleland points out that, in such embodiments, it is necessary to double the number of windings to obtain the same inductance that would be provided by a toroid having windings all of the same sense. Thus, reduced RT voltage stresses are obtained at the sacrifice of compactness. This particular inductor design has nevertheless been used extensively in commercial particle accelerators. The use of higher frequency RF generators would lead to a proportionate reduction in the size of their inductors and capacitors, but the limit for contemporary commercial generators used in continuous accelerators is in the range of 100–150 kHz.

SUMMARY OF THE INVENTION

One object of the present invention is to provide a compact, transportable, rugged, high power, high efficiency apparatus for irradiating a substrate, for example, for the radiation processing of solid or liquid materials.

Another object of the present invention is to provide an improved high voltage inductor suitable for use, inter alia, in a compact, transportable, rugged, high power, high efficiency apparatus for irradiating a substrate.

Another object of the present invention is to provide an improved power transfer apparatus for use, inter alia, in a compact, transportable, rugged, high power, high efficiency apparatus for irradiating a substrate.

One more object of the present invention is to provide an improved voltage multiplication apparatus for use, inter alia, in a compact, transportable, rugged, high power, high efficiency apparatus for irradiating a substrate.

One more object of the present invention is to provide an improved auxiliary power supply for use in voltage multiplication apparatus used, inter alia, in a compact, transportable, rugged, high power, high efficiency apparatus for irradiating a substrate.

Another object of the present invention is to provide an improved self-shielded, compact, transportable, rugged, high power, high efficiency apparatus for irradiating a substrate.

Yet another object of the present invention is to provide improved methods and apparatus for the radiation processing of solid or liquid materials.

In accordance with a first aspect of the principles of the present invention, an electrical apparatus for irradiating a substrate is provided comprising:

(i) a vacuum chamber including a transmission window which is located at a first end of the vacuum chamber;

(ii) a particle beam generator within the vacuum chamber; and (iii) a particle beam accelerator, within the vacuum chamber, which accelerates and directs particles from the generator towards and through the transmission window, the apparatus having at least one of the following characteristics:

(A) it comprises an inductor comprising:

(i) a pair of high voltage terminals, and (ii) a first inductive component having a first inductance and a second inductive component having a second inductance, the inductive components being spaced close together and substantially parallel to one another and each comprising a plurality of turns, the turns of the second inductive component being wound in an opposite clockwise sense to the turns in the first inductive component, and the turns of the first and second inductive components being electrically connected in series between the high voltage terminals to form the inductor, which has a total inductance and is so configured that the high voltage terminals are spatially remote from each other and the total inductance is greater than either the first inductance or the second inductance;

(B) it comprises a high voltage AC power transfer apparatus comprising at least one of:

(i) a transformer having a first coil, which forms part of a first resonant circuit having a high frequency selectivity (high Q), and a second coil, which forms part of a second resonant circuit having a high frequency selectivity and having a predetermined resonant frequency, the coupling between the first and second coils being close to or at the critical coupling value; or (ii) a phase locked loop generator, for generating a square wave electrical signal at a predetermined value of frequency and voltage, and at least one voltage gain solid state power driver connected to the generator for receiving and converting the square wave signal from the phase locked loop generator into a power signal having a square wave voltage profile, the driver being configured for connection to and for driving a first coil of a transformer;

(C) it comprises a voltage multiplication apparatus comprising:

(i) a first and a second metallic electrode, adapted to be connected to a source of AC power;

(ii) a ground connection and a high voltage DC terminal, (iii) a plurality of solid state rectifier units each having an anode and cathode, the units being positioned between the electrodes and being series-connected anode to cathode between the ground connection and the high voltage DC terminal, and (iv) a capacitor plate connected at each one of the electrical junctions thereby formed between the rectifier units;

a) each capacitor plate being independently positioned at its own predetermine spacing from one of the first electrode or the second electrode, and in combination with that electrode forming a capacitor having a predetermined capacitance, to form a plurality of capacitor modules each independently comprising at least one capacitor, b) the predetermined spacings increasing for successive capacitor modules, c) the capacitor plates being adapted to capacitively couple an AC potential of substantially equal amplitude across the capacitors via the capacitance between the capacitor plates and the electrodes, and d) the capacitance between a capacitor plate and an electrode being similar to an average value of capacitance between the capacitor plates and electrodes;

(D) the vacuum chamber comprises a drift tube which connects the particle accelerator to the first end of the vacuum chamber, the drift tube comprising vacuum connection means for connecting the vacuum chamber to vacuum pump means and, between the vacuum connection means and the first end of the vacuum chamber, a diversion chamber having:

(i) an entrance through which the particle beam enters the diversion chamber, (ii) an exit facing the first end of the vacuum chamber and being at a finite angle less than 180° to the longitudinal axis of the drift tube section at the entrance thereof; and (iii) means for redirecting and scanning the particle beam so that it is directed toward the exit, which comprises a widened section of drift tube connecting it to the first end of the vacuum chamber, thereby accommodating any trajectory variance of the scanned particle beam;

(E) it comprises an auxiliary power supply adapted for use with a voltage multiplication apparatus having:

(i) a pair of metallic electrodes adapted to be connected one each to opposing polarities of a source of AC power, (ii) a ground connection and a high voltage DC terminal, (iii) a plurality of solid state rectifier units each having an anode and cathode, the units being positioned between the electrodes and being series-connected anode to cathode between the ground and the high voltage DC terminal, (iv) a plurality of capacitor plates each spaced from one or the other of the electrodes, each of the electrical junctions thereby formed between the rectifier units being connected to one of said capacitor plates for capacitively coupling an AC potential of substantially equal amplitude across the capacitors via the capacitance thereby formed between the electrodes and the capacitor plates, (v) a transformer having a primary coil having first and second terminals, and a secondary coil having two terminals for providing auxiliary power, and (vi) the auxiliary power supply comprising a variable capacitor electrically connected in series between one of said capacitor plates and the first terminal of the primary coil of the transformer, and the second terminal of the primary coil being electrically connected to another capacitor plate; or (F) it comprises:

(a) a power generator, (b) a shielded vault comprising:

(i) an enclosure open at one end, and (ii) a door frame structure, comprising a door, removably secured to the open end of the enclosure, and (c) a baseguide structure attached to the shielded vault enclosure, means slidably mounting the door frame structure on the base guide structure, and the vacuum chamber being secured to the door frame structure, such that the door frame structure and door, when secured to the enclosure, encloses at least the vacuum chamber within the vault to provide self-shielding for the apparatus for irradiating a substrate, and, when moved away from the enclosure along the base guide structure, facilitates servicing and maintenance of the vacuum chamber.

In a second aspect, also in accordance with the principles of the present invention, an electrical apparatus is provided having at least one of the following characteristics:

(A) it comprises an inductor comprising:

(i) a pair of high voltage terminals, and (ii) a first inductive component having a first inductance and a second inductive component having a second inductance, the inductive components being spaced close together and substantially parallel to one another and each comprising a plurality of turns, the turns of the second inductive component being wound in an opposite clockwise sense to the turns in the first inductive component, and the turns of the first and second inductive components being electrically connected in series between the high voltage terminals to form the inductor, which has a total inductance and is so configured that the high voltage terminals are spatially remote from each other and the total inductance is greater than either the first inductance or the second inductance;

(B) it comprises a high voltage AC power transfer apparatus comprising:

a transformer having a first coil, which forms part of a first resonant circuit having a high frequency selectivity, and a second coil, which forms part of a second resonant circuit having a high frequency selectivity and having a predetermined resonant frequency, the coupling between the first and second coils being close to or at the critical coupling value, the first resonant circuit also comprising a phase locked loop generator, for generating a square wave electrical signal at a predetermined value of frequency and voltage, and at least one voltage gain solid state power driver connected to the generator for receiving and converting the square wave signal from the phase locked loop generator into a power signal having a square wave voltage profile, the driver being connected to and driving the first coil of the transformer, and the second resonant circuit transforming the square wave voltage profile power signal from the first coil into continuous substantially sinusoidal high voltage electrical power in the second resonant circuit, and also comprising an electrical power load;

(C) it comprises a voltage multiplication apparatus comprising:

(i) a first and a second metallic electrode, adapted to be connected to a source of AC power;

(ii) a ground connection and a high voltage DC terminal, (iii) a plurality of solid state rectifier units each having an anode and cathode, the units being positioned between the electrodes and being series-connected anode to cathode between the ground connection and the high voltage DC terminal, and (iv) a capacitor plate connected at each one of the electrical junctions thereby formed between the rectifier units;

a) each capacitor plate being independently positioned at its own predetermined spacing from one of the first electrode or the second electrode, and in combination with that electrode forming a capacitor having a predetermined capacitance, to form a plurality of capacitor modules each independently comprising at least one capacitor, b) the predetermined spacings increasing for successive capacitor modules, c) the capacitor plates being adapted to capacitively couple an AC potential of substantially equal amplitude across the capacitors via the capacitance between the capacitor plates and the electrodes, and d) the capacitance between a capacitor plate and an electrode being similar to an average value of capacitance between the capacitor plates and electrodes;

(D) it comprises an auxiliary power supply adapted for use with a voltage multiplication apparatus having:

(i) a pair of metallic electrodes adapted to be connected to a source of AC power, (ii) a ground connection and a high voltage DC terminal, (iii) a plurality of solid state rectifier units each having an anode and cathode, the units being positioned between the electrodes and being series-connected anode to cathode between the ground and the high voltage DC terminal, (iv) a plurality of capacitor plates each spaced from one or the other of the electrodes, each of the electrical junctions thereby formed between the rectifier units being connected to one of said capacitor plates for capacitively coupling an AC potential of substantially equal amplitude across the capacitors via the capacitance thereby formed between the electrodes and the capacitor- plates, (v) a transformer having a primary coil having first and second terminals, and a secondary coil having two terminals for providing auxiliary power, and (vi) the auxiliary power supply comprising a variable capacitor electrically connected in series between the one of said capacitor plates and a terminal of the primary coil of the transformer, and the other primary terminal being electrically connected to the high voltage terminal.

As used earlier hereinabove, the word “turn”, when used in this specification in the singular, means a single open ended 360° loop or winding of electrically conductive material and, when used in the plural, means a plurality of such loops or windings having direct or indirect electrical connections.

One facet of both these aspects of this invention provides an apparatus comprising an inductor which comprises at least two inductive components, wherein:

i) the first inductive component has a predetermined length and comprises a predetermined number of conductor turns, divided into a plurality of first sequences, each one of which comprises one or more conductor turns, each turn having a predetermined shape; and (ii) the second inductive component, adjacent to and substantially parallel to the first inductive component, has a predetermined length and number of turns, which is substantially similar to that of the first inductive component, and comprises a predetermined number of conductor turns divided into a plurality of second sequences each one of which comprises one or more conductor turns substantially identical in shape to those of the first inductive component but opposite in winding sense;

each one of the first sequences being series connected end to end with at least one second sequence and each one of the second sequences being series connected end to end with at least one first sequence to form an electrically conductive path which alternates between the first and second inductive components;

such that the inductive contribution of a sequence of conductor turns is 25% or less of the total inductance of the inductor.

More preferably, the inductive contribution of a sequence of conductor turns is 10% or less of the total inductance of the inductor, for example 5% or less. Most preferably, the inductive contribution of a sequence of conductor turns is 2% or less of the total inductance of the inductor, for example 1% or less. Preferably, the number of turns in a sequence of conductor tuns between successive alternations is less than 11. More preferably, the number of turns in a sequence of conductor turns between successive alternations is less than 6, for example, less than 4. Most preferably, the number of turns in a sequence of conductor turns between successive alternations is less than 3, for example, 1.

Preferably, the number of turns in each one of the alternate sequences of conductor turns is equal and the total number of turns in the inductor is even. Preferably, each one of the first and second inductors is in the general form of a cylinder halved longitudinally along a diameter, that is, each conductor turn of either inductor component is D-shaped and the two inductor components are positioned face to face along the diametrical faces of the half cylinder so that the inductor components abut and the sections of a turn that transition (alternate) from one inductive component to the other are common to both inductive components.

Preferably, the conductor turns are formed of Litz wire.

Preferably, the high voltage AC power transfer apparatus of the first aspect of the invention comprises both the transformer and the phase locked loop generator, which is connected, preferably through a signal processor means, to at least one voltage gain solid state power driver.

As a further facet of both these aspects of the present invention, the second resonant circuit of the high voltage AC power transfer apparatus, for transform the power signal pulses having a square wave voltage profile from the first coil into continuous substantially sinusoidal high voltage electrical power in the second resonant circuit, also comprises an electrical power load. The coupling between the first and second coil of the transformer is recommended to be in the range of 0.75 to 1.1 times the critical coupling value, and preferably, 0.9 to 1.05 times the critical coupling value. Preferably, in both the first and second aspects of the invention, the high voltage AC power transfer apparatus comprises an electrical feedback connection, between the second resonant circuit and the phase locked loop generator, for maintaining the frequency of the square wave electrical signal at the predetermined resonant frequency. Preferably, the solid state power driver is energized by a variable preselected voltage supplied from a power generator comprising one or more silicon controlled rectifiers. Preferably, the apparatus also includes a shut down latching circuit connected between the phase locked loop generator and each one of the solid state power drivers for rapidly shutting down the electrical apparatus in the event of an out-of-specification load condition. These feedback connections ensure that triggering of the latching circuit by an out of speicfication load condition results in the shutting down of the power generator within one line frequency cycle and the solid state power driver within less than 10, preferably less than 5 cycles of the predetermined resonant frequency.

As still a further facet of the voltage multiplication apparatus embodiments of both the first and second aspects of the present invention, the predetermined spacings preferably increase in substantially equal steps for successive capacitor modules, and the capacitance between a capacitor plate and an electrode preferably is substantially identical to an average value of capacitance between the capacitor plates and electrodes. Preferably, the voltage multiplication apparatus is so configured that:

(i) a first capacitor having a capacitor plate for receiving the AC potential is positioned in a first capacitor module at a first predetermined distance from the nearest electrode, and (ii) a second capacitor having a capacitor plate for receiving the AC potential is positioned in a second capacitor module, placed immediately adjacent to the first capacitor module, at a second predetermined distance from the nearest electrode, the second predetermined distance being from 1.05 times to twice as large as the first predetermined distance.

The lower limit to the ratio is set by the number of modules, which in the above embodiment is about 20. If the voltage multiplier has, say, 10 modules, the second predetermined distance is advantageously from 1.1 times to twice as large as the first predetermined distance. In a voltage multiplier with fewer than 10 modules the second predetermined distance may be from 1.15 times to twice as large as the first predetermined distance, for example, the second predetermined distance may be at least 1.2 times as large as the first predetermined distance.

Preferably also, the voltage multiplication apparatus is so configured that:

(i) a first capacitor having a capacitor plate for receiving the AC potential is positioned in a first capacitor module at a first and smallest predetermined distance from the nearest electrode, and (ii) a second capacitor having a capacitor plate for receiving the AC potential is positioned in a second capacitor module at a second and largest predetermined distance from the nearest electrode, the second predetermined distance being at least 1.5 times as large as the first predetermined distance.

More preferably, the second predetermined distance is at least twice as large as the first predetermined distance. More preferably, yet, the second predetermined distance is at least 3 times as large as the first predetermined distance, for example, the second predetermined distance is at least 4 times as large as the first predetermined distance.

Adjacent capacitor plates may be provided with spark gaps adjacent to the electrical junctions between the plurality of rectifier units. Also, each rectifier unit is preferably provided, at each junction, with means for dissipating transient voltage and current surges. Such means may include, but is not limited to, inductors which become lossy at very high frequencies (e.g., ten or more times the highest operating frequency), and are placed in the connection means between each rectifier unit and the electrical junction, which have negligible impedance at the predetermined resonant frequency but a large impedance at a frequency at least 10 times the resonant frequency, preferably, at a frequency at least 100 times the resonant frequency. Preferably, such means comprise, for example, ferrite attenuator beads surrounding the conductor leads from each rectifier unit to an electrical junction. Each head may also be shunted by a small resistance (e.g., 1000 Ω), if desired, should corona problems arise around the beads.

In certain circumstances, for example, when the AC voltage supplied to the two electrodes is very high, it is advantageous that one capacitor constitute each capacitor module. In this embodiment it is advantageous for the metallic electrodes to be spaced apart and formed into semi-cylindrical surfaces elongated along a common axis. Each capacitor plate is then formed into a segment of a cylindrical surface facing one of the electrodes, each plate at its own predetermined spacing so that successive capacitor plates are:

(i) electrically connected together via a rectifier unit, (ii) serially arrayed between ground and a high voltage terminal, and (iii) serially arranged around the common axis to face one or the other of the electrodes, the predetermined spacings increasing in substantially equal steps for each successive capacitor. Thus the capacitor plates are arranged in stepwise fashion, the height of each successive step increasing along a spiral whose radius decreases as the number of rectifier units between the capacitor plate and ground increases.

As a further facet of the first and second aspects of the present invention, one of the secondary coil terminals of the auxiliary power supply in a preferred embodiment is connected to the high voltage terminal capacitor plate. Preferably, the secondary coil of the transformer used in the auxiliary power supply is shunted by back-to-back Zener diodes to maintain a minimum power load on the secondary circuit. Preferably, the first capacitor plate is connected to the variable capacitor. In another preferred embodiment, the secondary coil is connected to and supplies electrical power to an electron emitter to heat it.

In either the first or the second aspect of the invention, more preferred embodiments comprise at least two of the characteristics set forth therein, yet more preferred embodiments comprise at least three of the characteristics set forth therein, and highly preferred embodiments comprise at least four of the characteristics set forth therein. Most preferred embodiments comprise each one of the characteristics set forth therein.

In a preferred embodiment of the diversion chamber of the first aspect of the invention, the section of the drift tube, between the vacuum connection means and the diversion chamber, is provided with a diaphragm normal to the axis of the drift tube at that point, the diaphragm having an orifice at the center thereof to permit easy passage of the particle beam therethrough. Advantageously, the diversion chamber is further provided with a blind tube or recess in a wail thereof facing the first end of the vacuum chamber whereby material entering the chamber is trapped in the blind tube or recess and thereby prevented from further damaging the particle accelerator or the vacuum pump means. These embodiments of the first aspect of the invention are of particular utility in applications in which there is a risk of failure or puncture of the transmission window at the first end of the housing, which would otherwise lead to contamination of the interior of the vacuum chamber and damage to the particle accelerator tube or vacuum pump means, for example by liquid or solid material. If such materials gain entry to the diversion chamber through implosion of the transmission window foil, their inertia will cause most of this debris to impact on the facing wall of the blind tube or recess in the diversion chamber rather than exiting through the drift tube towards the vacuum connection means and the particle accelerator. The orifice in the diaphragm serves to restrict fluid flow from the diversion chamber thus further reducing damage to the accelerator section and vacuum pump means in such an event.

A third aspect of the invention provides an inductor element, for use in high voltage inductors, having a first end and a second end and comprising a central segment with a predetermined length, a first longitudinal edge, and a second longitudinal edge, and further comprising one of:

(i) a first arcuate segment depending from the first edge and a second arcuate segment depending from the second edge, the first arcuate segment and the second arcuate segment being substantially coplanar with but at opposite ends of the rectangular segment, each arcuate segment having (a) a width from 0.8 to 5 times that of the rectangular segment, (b) an outer radius of at least a part of the arcuate segment taken from a center point, which is from 0.25 to 0.75 times the length of the rectangular segment, and (c) a first end, at a longitudinal edge of the rectangular segment, and a second end;

the first and second ends of each arcuate segment subtending at the center point an arc of at least 90°;

(ii) a first 'L' shaped segment depending from the first edge and a second 'L' shaped segment depending from the second edge, the first 'L' shaped segment and the second 'L' shaped segment being substantially coplanar with but at opposite ends of the rectangular segment, each 'L' shaped segment having (a) a width from 0.8 to 5 times that of the rectangular segment, and (b) a total length which is from 0.75 to 1.25 times the length of the rectangular segment, and (c) a first end, at a longitudinal edge of the rectangular segment, and a second end;

the first and second ends of each 'L' shaped segment subtending at the center of the rectangular segment an arc of at least 90°;

(ii) a first substantially linear segment depending from the first edge and a second substantially linear segment depending from the second edge, the first substantially linear segment and the second substantially linear segment being substantially coplanar with but at opposite ends of the rectangular segment, each substantially linear segment having (a) a width from 0.8 to 5 times that of the rectangular segment, and (b) a total length, which is from 0.55 to 0.95 times the length of the rectangular segment, and (c) a first end, at a longitudinal edge of the rectangular segment, and a second end;

the first and second ends of each substantially linear segment subtending at the center of the rectangular segment an arc of at least 90°.

In the preferred embodiment, the inductor elements are wire-like conductors, for example Litz wire, supported on, and held in the desired shape by, a suitably configured frame.

In another embodiment, the inductor elements are laminar conductors, each of which is monolithic. In this embodiment, the inductor of the first and second aspects of the invention is formed from a series of such elements affixed together by securing a second end of an arcuate segment of a first laminar inductor element to a first end of an arcuate segment of the next laminar inductor element using, for example, bolts, welds or soldered joints. These laminar inductor elements are secured together to form the inductor of the invention in such a way that the rectangular central segments of the laminar inductor elements are superimposed in projection on one another.

As a fourth aspect of the present invention, a method in an electrical apparatus for providing high voltage substantially sinusoidal electrical power for an electrical load comprises the steps of:

generating a square wave electrical voltage signal pulse in a first high selectivity resonant circuit, which comprises a primary coil of a transformer, and which is tuned at a predetermined resonant frequency;

amplifying the square wave voltage signal pulse to drive the primary coil of the transformer;

transforming the square wave voltage signal pulse into high voltage substantially sinusoidal electrical power in a second resonant circuit, which comprises a secondary coil of the transformer having a high selectivity and being tuned to a second predetermined resonant frequency;

the coupling between the primary coil and the secondary coil of the transformer being close to or at the critical coupling value; and performing at least one of the following steps:

(i) using a portion of the substantially sinusoidal high voltage electrical power to regulate and maintain at a predetermined voltage the electrical power delivered to the electrical load, or (ii) using a portion of the substantially sinusoidal high voltage clerical power to maintain the predetermined frequency substantially at the resonant frequency of the second resonant circuit.

Preferably, the high voltage AC power transfer apparatus of the first aspect of the invention comprises both the transformer and the phase locked loop generator, which is connected, preferably through a signal processor means, to at least one voltage gain solid state power driver. Preferably the coupling between the first and second coil of the transformer is at or near the critical coupling value.

As a fifth aspect of the present invention, a method is provided for forming a high voltage inductor along a longitudinal dimension comprising:

(A) providing a plurality of first inductor elements each having a first end and a second end and comprising a central rectangular segment with a predetermined length and width, a first longitudinal edge and a second longitudinal edge, and further comprising one of:

(i) a first arcuate segment depending from the first edge and a second arcuate segment depending from the second edge, the first arcuate segment and the second arcuate segment being substantially coplanar with, but at opposite ends of, the rectangular segment, each arcuate segment having (a) a width from 0.8 to 5 times that of the rectangular segment, and (b) an outer radius of at least a part of the arcuate segment taken from a center point, which is from 0.25 to 0.75 times of the length of the rectangular segment, and (c) a first end, at a longitudinal edge of the rectangular segment and a second end;

the first and second ends of each arcuate segment subtending at the center point an arc of at least about 90°;

(ii) a first 'L' shaped segment depending from the first edge and a second 'L' shaped segment depending from the second edge, the first 'L' shaped segment and the second 'L' shaped segment being substantially coplanar with but at opposite ends of the rectangular segment, each 'L' shaped segment having (a) a width from 0.8 to 5 times that of the rectangular segment, and (b) a total length which is about equal to the length of the rectangular segment, and (c) a first end, at a longitudinal edge of the rectangular segment and a second end;

the first and second ends of each 'L' shaped segment subtending at the center of the rectangular segment an arc of at least about 90°; or (iii) a first substantially linear segment depending from the first edge and a second substantially linear segment depending from the second edge, the first substantially linear segment and the second substantially linear segment being substantially coplanar with but at opposite ends of the rectangular segment, each substantially linear segment having (a) a width from 0.8 to 5 times that of the rectangular segment, and (b) a total length which is about equal to half the length of the rectangular segment, and (c) a first end, at a longitudinal edge of the rectangular segment and a second end;

the first and second ends of each 'L' shaped segment subtending at the center of the rectangular segment an arc of at least about 90°;

(B) providing a plurality of second inductor elements each one of which is substantially a mirror image of a one of the first inductor elements; and (C) securing in end to end alternating and consecutive relation said first and said second inductor elements so that the projections of the rectangular segments of adjacent inductor elements are substantially superimposed along the longitudinal dimension of the inductor.

As a sixth aspect of die present invention, there is provided a method of operating a voltage multiplication apparatus which includes:

(i) a first and a second metallic electrode, (ii) a source of AC power connected to the electrodes, (iii) a plurality of solid state rectifier units each having an anode and cathode, the units being positioned between the electrodes and being series-connected anode to cathode between ground and a high voltage DC terminal, and (iv) a capacitor plate connected at each one of the electrical junctions thereby formed between the rectifier units;

a) each capacitor plate being independently positioned at its own predetermined spacing from one of the first electrode or the second electrode, and in combination with such electrode forming a capacitor having a predetermined capacitance, whereby a plurality of capacitor modules is formed each independently comprising at least one capacitor, b) the capacitor plates capacitively coupling an AC potential of substantially equal amplitude across the capacitors via the capacitance between the capacitor plates and the electrodes, c) the predetermined spacings increasing for successive capacitor modules, and d) the capacitance between a capacitor plate and an electrode being similar to an average value of capacitance between the capacitor plates and electrodes;

the method comprising:

applying AC electrical power to the first and second electrodes such that the electrical field gradient thereby formed between a capacitor plate and the corresponding electrode is similar to an average value of the electrical field gradient formed between all the capacitor plates and their corresponding electrodes.

Preferably, the electrical field gradient thereby formed between a capacitor plate and the corresponding electrode has a value between 0.4 times and 1.6 times an average value of the electrical field gradient formed between all the capacitor plates and their corresponding electrodes. More preferably, the electrical field gradient thereby formed between a capacitor plate and the corresponding electrode has a value between 0.7 and 1.3 times an average value of the electrical field gradient formed between all the capacitor plates and their corresponding electrodes. More preferably, yet, the electrical field gradient thereby formed between a capacitor plate and the corresponding electrode has a value between 0.8 and 1.2 times an average value of the electrical field gradient formed between all the capacitor plates and their corresponding electrodes. Most preferably, the electrical field gradient thereby formed between a capacitor plate and the corresponding electrode has a value between 0.9 and 1.1 times an average value of the electrical field gradient formed between all the capacitor plates and their corresponding electrodes.

As a seventh aspect of the present invention, a method is provided for protecting from damage an apparatus for irradiating a substrate, which includes:

(i) a vacuum chamber including a transmission window which is located at a first end of the vacuum chamber, (ii) a particle beam generator within the vacuum chamber, and (iii) a particle beam accelerator tube, within the vacuum chamber, which accelerates and directs particles from the generator towards and through the transmission window, the method comprising:

with a drift tube in the vacuum chamber, connecting the particle accelerator to the first end of the vacuum chamber, the drift tube having vacuum connection means for connecting the vacuum chamber to vacuum pump means and, between the connection means and the first end of the vacuum chamber, a diversion chamber, having an exit and entrance, the exit facing the first end of the vacuum chamber and being at a finite angle less than 180° to the longitudinal axis of the drift tube segment at the entrance through which the particle beam enters the diversion chamber;

generating a particle beam within the particle beam generator;

accelerating and directing the particle beam from the generator toward the entrance of the diversion chamber; and redirecting the particle beam which enters the diversion chamber through a finite angle less than 180° to direct it toward the first end of the vacuum chamber.

Preferably, the particle beam is directed through an orifice in a diaphragm placed in a segment of the drift tube, which is between the particle accelerator and the diversion chamber. Preferably, the particle beam is scanned as well as redirected within the diversion chamber.

Most preferably, in all aspects and embodiments of both the apparatuses and methods of the invention, the apparatus for irradiating a substrate is an electron accelerator apparatus, the particle generator is an electron emitter and the particle accelerator is an electron accelerator tube.

As an eighth aspect of the present invention, a method is provided for providing auxiliary power for use with a voltage multiplication apparatus having:

(i) a pair of metallic electrodes, adapted to be connected to a source of AC power, (ii) a plurality of solid state rectifier units each having an anode and cathode, the units being positioned between the electrodes and being series-connected anode to cathode between ground and a high voltage DC terminal, and (iii) a plurality of capacitor plates, one being connected at each of the electrical junctions thereby formed between the rectifier units, for capacitively coupling from sad electrodes an AC potential of substantially equal amplitude across successive capacitors via the capacitance thereby formed between the electrodes and the capacitor plates; the method comprising:

capacitively tapping off electrical power from one of the capacitor plates via a variable capacitor electrically connected in series between that capacitor plate and a first terminal of a primary coil of a transformer, a second terminal of the primary coil being electrically connected to another capacitor plate such as the high voltage output terminal; and obtaining the auxiliary electrical power from two terminals of a secondary coil of the transformer.

As a ninth aspect of the present invention, a method is provided for gaining access to a self-shielded apparatus for irradiating a substrate which includes:

(a) a power generator, (b) a particle accelerator, and (c) a shielded vault comprising an enclosure open at one end and a door frame structure comprising a door removably secured to the open end of the enclosure; the method comprising:

movably mounting the door frame structure on a guide structure which is attached to the shield vault enclosure, securing the particle accelerator to the door frame structure, securing the door frame structure and door to the enclosure to enable secure operation of the particle accelerator apparatus, and moving the door frame structure and door away from the enclosure along the guide structure to facilitate servicing and maintenance of the apparatus.

BRIEF DESCRIPTION OF THE DRAWINGS

In the Drawings:

FIGS. 4*b* and 4*c* illustrate plan and end views, respectively, of the primary coil of the transformer shown in FIG. 4*a*.

DETAILED DESCRIPTION OF PREFERRED EMBODIMENTS

Figure 1:
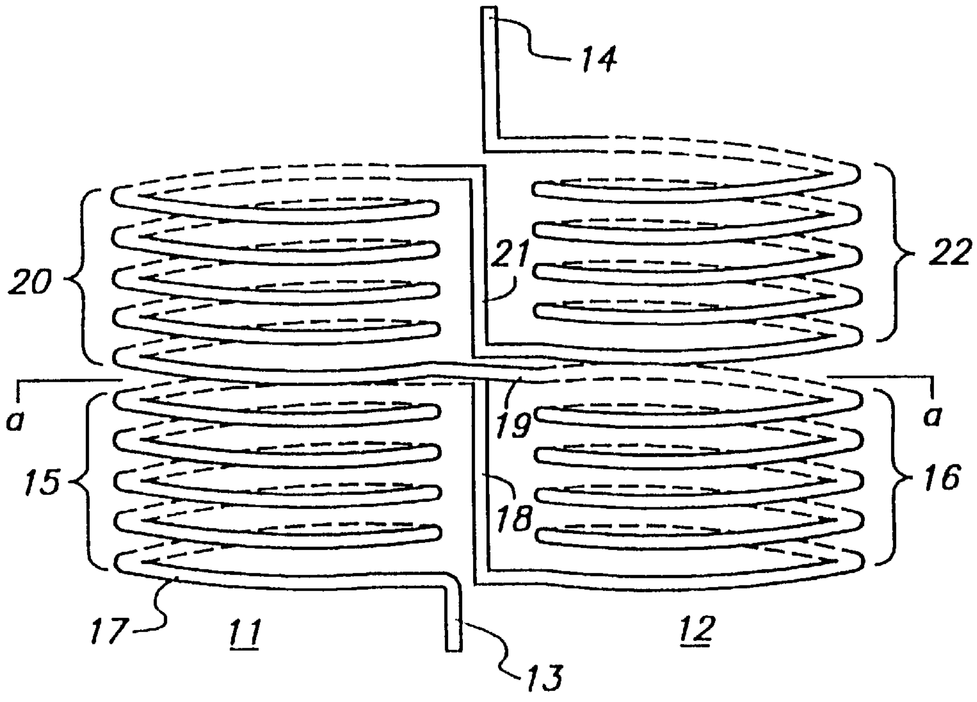
FIG. 1 illustrates diagrammatically an embodiment of the inductor of the invention containing two inductive components, in which five turns of conductor in one inductive component in a clockwise sense is followed by five turns of conductor in the other inductive component in an anticlockwise sense.

FIG. 1 illustrates an improved inductor comprising a first inductive component 11 and a second inductive component 12, which as compared with a toroidal inductor has substantially reduced radio frequency voltage stress between the opposite polarity terminals 13 and 14. Using the terms "clockwise" and "anti-clockwise" to denote simply the relative senses of the turns, the improved inductor is achieved by forming sequential sets of 5 clockwise conductor turns to form a segment 15 of first inductive component 11 and five anti-clockwise conductor turns to form a segment 16 of second inductive component 12. Conductor 17 is wound for five substantially circular turns in a clockwise sense to form segment 15, then is transitioned through connecting link 18 to the second inductive component 12 and wound for 5 substantially circular turns in an anti-clockwise sense to form segment 16. The conductor then transitions back to first inductive component 11 through connecting link 19 and is wound for 5 substantially circular turns in a clockwise sense to form segment 20 before transitioning again through connecting link 21 to be wound for 5 substantially circular turns in an anti-clockwise sense to form segment 22. Because the ends of the two linear solenoids thereby formed are very close together and opposite in magnetic polarity any magnetic field generated is closely confined within the inductive components 11 and 12, and to the regions immediately adjacent to the ends of the inductive components 11 and 12. Furthermore, the opposite polarity terminals at 13 and 14 are at opposite ends of the inductor so that RF electric field stress between them is low.

Figure 2:
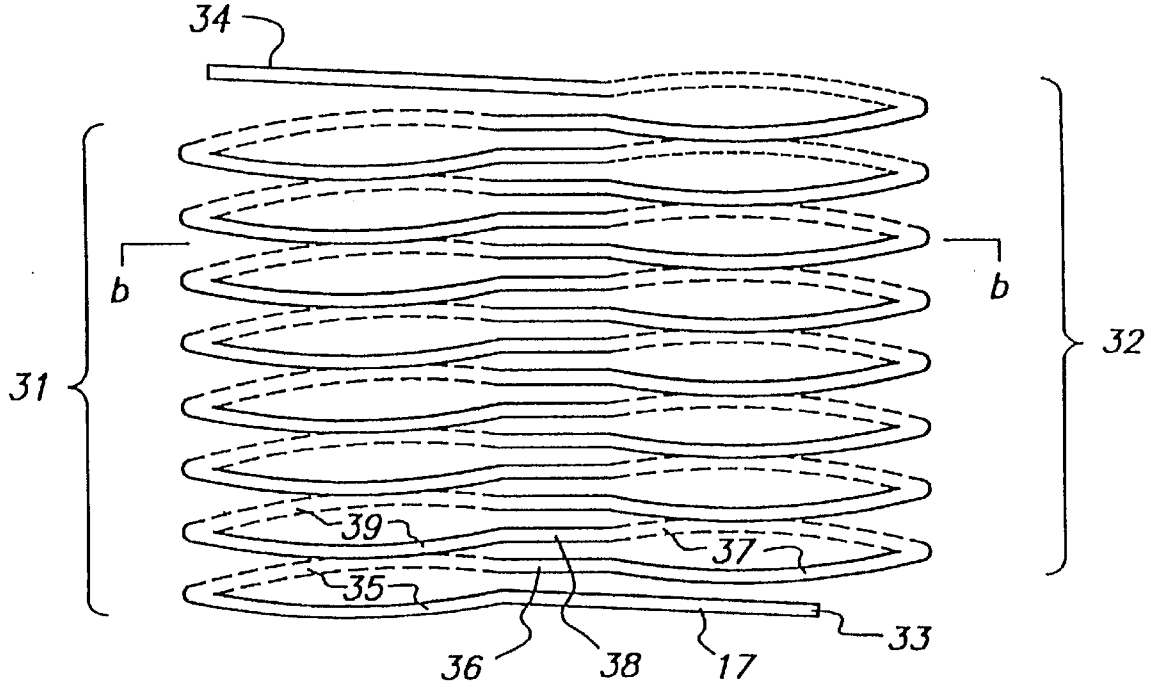
FIG. 2 illustrates diagrammatically an embodiment of the inductor of the invention containing two inductive components, in which each turn of conductor in one inductive component in a clockwise sense is followed by a turn of conductor in the other inductive component in an anticlockwise sense and vice versa.

FIG. 2 illustrates a preferred embodiment of the inductor wherein successive turns alternate between the first inductive component and the second inductive component. The inductor comprises inductive components 31 and 32 and opposing polarity terminals 33 and 34. Conductor 17 is wound for one circular turn 35 in a clockwise sense in inductive component 31 then transitions through connecting link 36 to be wound for one circular turn 37 in an anti-clockwise sense in inductive component 32 and then transitions again through connecting link 38 to form another clockwise turn 39 in inductive component 31. In this way 10 turns in all are wound in alternating fashion in each of inductive components 31 and 32. Although both FIGS. 1 and 2 illustrate substantially circular turns in the inductive components it is to be understood that the projection of the shape of the turns on a plane transverse to the longitudinal dimension of the inductor may be in the form of paired ellipses or paired squares or paired triangles or paired parallelograms (such a transverse plane is indicated by the dotted line a . . . a in FIG. 1 and b . . . b in FIG. 2). As with FIG. 1, in FIG. 2, because the ends of the two linear solenoids thereby formed are very close together and opposite in magnetic polarity, any magnetic field generated is confined within the inductive components 31 and 32 and closely confined to the regions immediately adjacent to the ends of the inductive components 31 and 32. Likewise, because opposite polarity terminals at 33 and 34 are spatially remote, at opposite ends of the inductor, RF electric field stress between them is low.

Figure 3A:
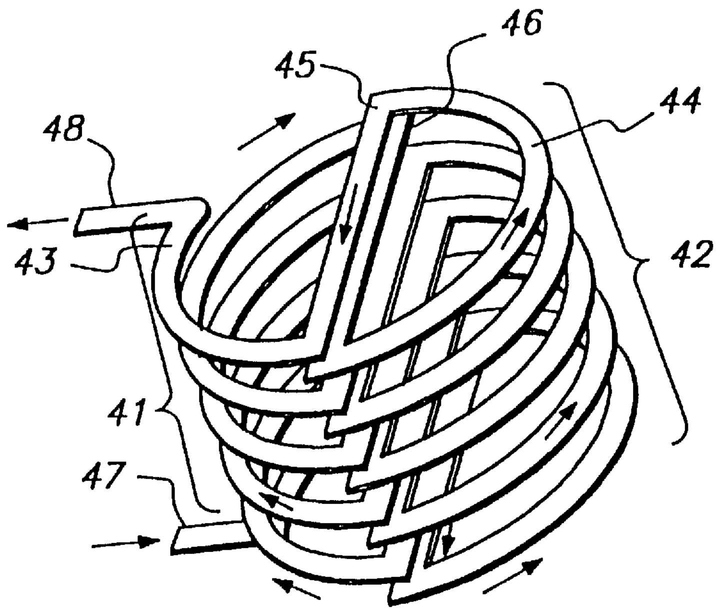
FIG. 3*a* illustrates diagrammatically a preferred embodiment of the inductor of the invention containing two D-shaped inductive components, in which every turn of conductor in one inductive component in a clockwise sense is followed by a turn of conductor in the other inductive component in an anticlockwise sense and vice versa.
Figure 3B:
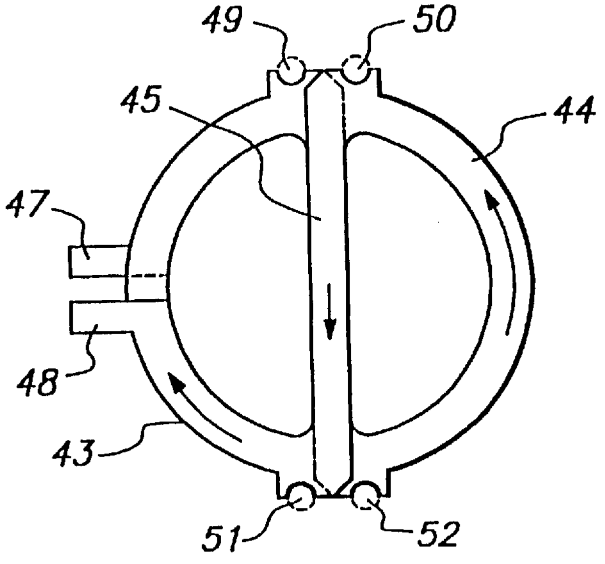
FIG. 3*b* is a more particular cross-sectional illustration of an embodiment of the inductor like that shown diagrammatically in FIG. 3*a*.

FIG. 3*a* illustrates diagrammatically a more preferred embodiment of the inductor wherein successive turns alternate between a first inductive component 41 and a second inductive component 42. As is shown with greater particularity in FIG. 3*b*, the projection of the shape of a clockwise turn 43 in inductive component 41 is generally that of a reversed capital letter D and the shape of an anti-clockwise turn 44 in inductive component 42 is generally that of a capital letter D. Note that in this embodiment, separate connecting links between alternating turns are not needed as the straight legs, for example 45 and 46, of the normal or reversed D shaped turns are common to both inductive components. This is a considerable advantage as these legs thereby contribute to the inductance of both inductive components, whereas portions of the connecting links in FIGS. 1 and 2 contribute to one or the other inductive component or to neither but not to both. As this embodiment, like the previous embodiments, locates the opposite polarity voltage terminals at opposite ends of the inductor, the RF field stress between these two terminals 47 and 48 of the inductor is reduced to a very low value. The direction of winding of conductor in inductive components 41 and 42 is indicated by the arrows within FIGS. 3*a* and 3*b*. The conductor of FIGS. 3*a* and 3*b* is rectangular in cross section, but any geometrical form of conductor may be used, such as circular in cross section, as shown in the preferred embodiment illustrated in FIGS. 4*d* and 4*e*. Thus the conductor may be metal in the form of a rod (solid conductor) or may be stranded or in the form of a hollow tube or Litz wire, as well. A particular advantage of the solid rectangular conductor of these figures is that it may be easily fabricated from rectangular segments and C-shaped or otherwise shaped segments which can be welded or otherwise joined together, for example, by bolting together. In one embodiment the component segments are supported by 4 insulating support rods at the junction of the straight and curved segments, as indicated by the dotted circles 49, 50, 51 and 52 in FIG. 3*b* and, in the middle of the curved segments, by a comb-like insulating dielectric array (not shown) whose teeth interdigitate between successive turns. For use at high frequencies, it is advantageous that the solid rectangular conductor have a depth which is not substantially greater than three times the “skin depth” of the RF current at that frequency. To increase the mechanical rigidity of such rectangular conductors, the conductor is preferably creased or provided with stiffening ribs along its length.

Preferably, an inductive component has an air core, although in certain circumstances (for example if a very compact design is required) a ferrite or other suitable core material may be used. Preferably, an inductive component is substantially linear along its dimension, although in certain circumstances (for example if a very compact design is required) a curved or otherwise convoluted shape along the dimension of the component may be utilized.

Figure 4A:
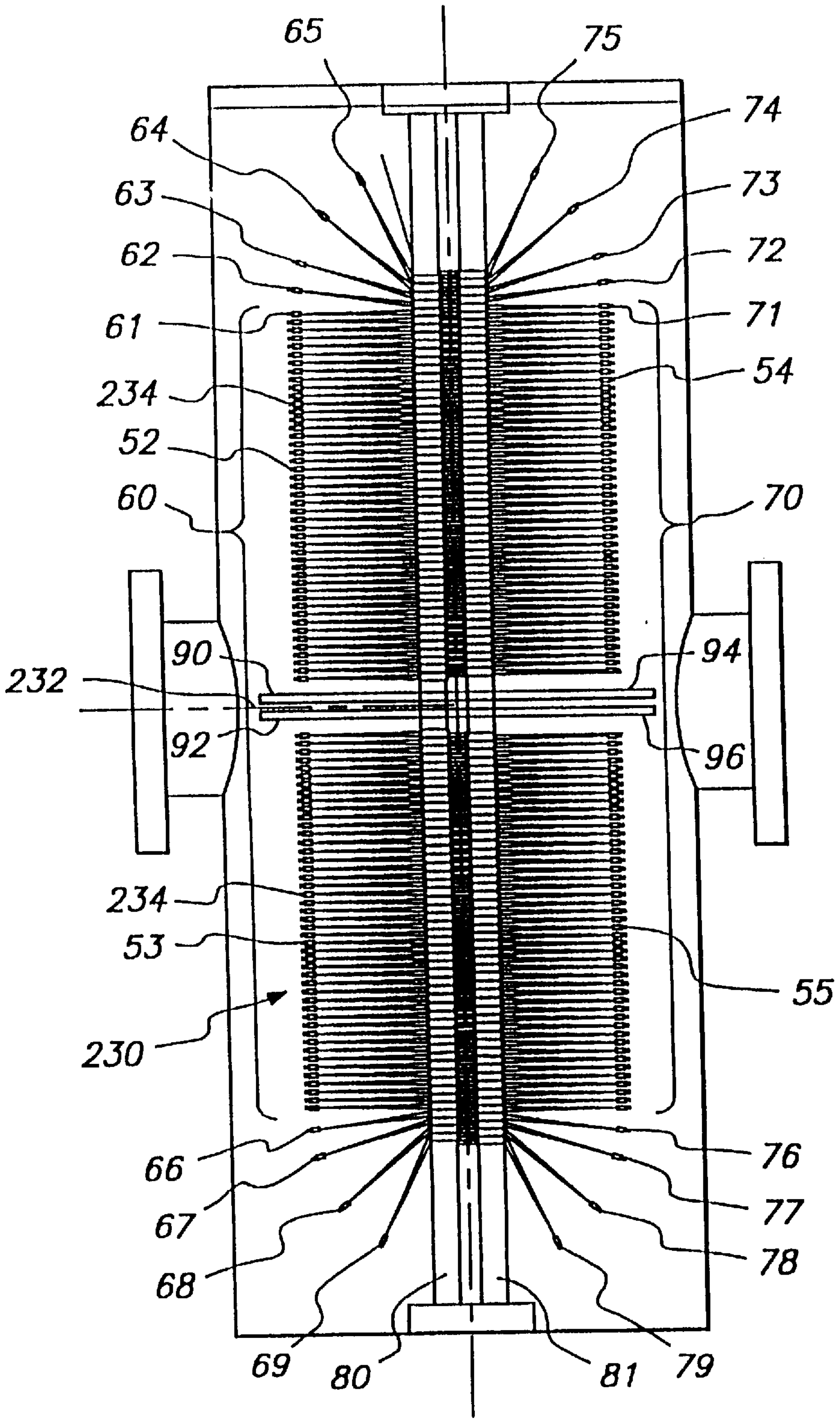
FIG. 4*a* illustrates diagrammatically an embodiment of the invention wherein the inductor of the invention is configured as a transformer.
Figure 6:
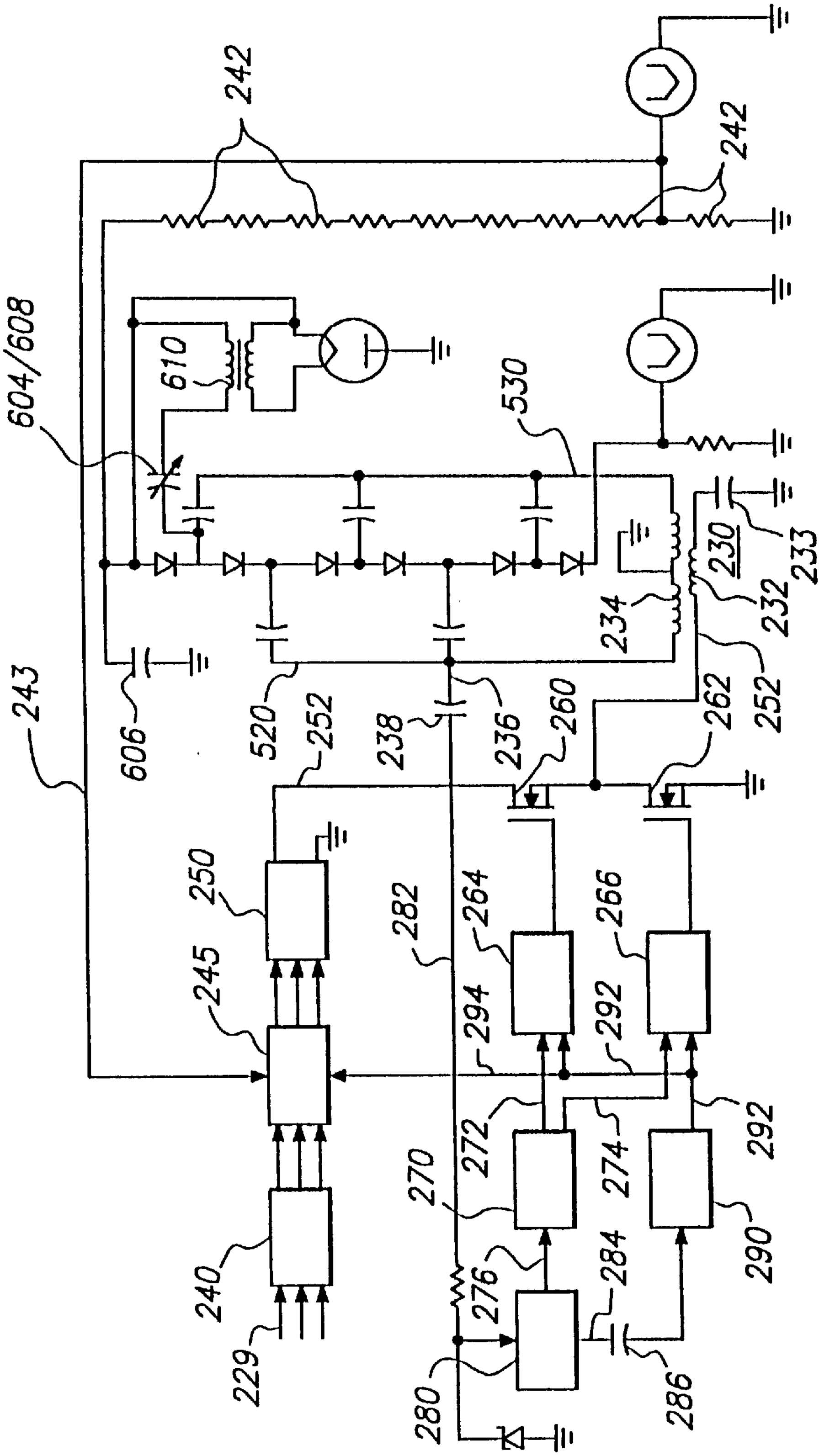
FIG. 6 is a block circuit diagram of an embodiment of the high voltage generator, controls, and accelerator incorporating the inductor of the invention.

Certain embodiments employ the inductor of this invention to provide one or more coils of a transformer 230 (FIG. 6). Advantageously, both the primary 232 and the secondary 234 coils of the transformer comprise inductors of the invention. One embodiment of this aspect of the invention is shown in FIG. 4*a* and is of particular utility when the circuit comprising the primary of the transformer is energized by triggering pulses. The individual turns in FIG. 4*a* preferably have the general shape depicted in FIGS. 3*a* and 3*b*, that is they are preferably ‘D’ shaped. The inductive components 60 and 70, which form the secondary turns of the transformer, are each composed of two sub-units: 52 and 53 for inductive component 60, and 54 and 55 for inductive component 70. Each sub-unit may comprise from 1 to 100 turns and in this particular Figure each sub-unit comprises 50 turns. Between these subunits lie two primary coils comprising turns 90 and 94, and 92 and 96. For example, using this preferred “figure-of eight” configuration, especially in the “D” shaped embodiment, each primary may consist of a single figure-of-eight structure thus providing one turn for each secondary inductive component. In this way very high voltage ratios between primary and secondary circuits may be obtained. The turns of the inductors are secured between a plurality of insulating rods, two of which, 80 and 81, are depicted in FIG. 4*a*. These rods are formed of a low dielectric loss material such as a polymeric material having slots therein to receive and support the turns.

Referring to any of FIGS. 1 to 4*a*, it will be seen that the turns of inductive component 11 and 12, 31 and 32, 41 and 42 and 60 and 70 form sets of corresponding turns. That is, corresponding turns, for example 61 and 71 of FIG. 4*a*, lie at the same level or in the same plane (a corresponding plane) of the inductor. They are also normally at an angle of 180° to one another. Advantageously, however, corresponding sets of turns approaching the ends of the inductor are formed to lie at an angle to each other which becomes more acute as each end of the inductor is approached. In this manner and referring again to FIG. 4*a*, they form transitions having the shape of a segment of a toroid at each end of an otherwise non-toroidal inductor comprising inductive components 60 and 70. These toroidally shaped transitions, comprising the turn sets 62 and 72, 63 and 73, 64 and 74, and 65 and 75 at a first end of the inductor and 66 and 76, 67 and 77, 68 and 78, and 69 and 79 at a second end of the inductor, serve to channel the RF magnetic flux from one inductive component to the other. As their main function is not to increase the inductance of either inductive component, but simply to control and limit any leakage of the magnetic flux at each end of an inductive component, it is not necessary to position these transition turns as close together as in the main bulk of an inductive component. In fact, it is only necessary that these turns be close enough at their (radially) outer side that the leakage fields between the turns at the ends be reduced to a desired level, which is usually a level at which such fields are insignificant when compared with the flux within the inductor.

Thus, the inductor has a first end and a second end, and has a first set of corresponding turns at least at one of the ends, a second set of corresponding turns adjacent to, but separated from that end by the first set, and a corresponding third set, fourth set, fifth set and so on to a maximum preferably of not more than ten sets of corresponding turns consecutively further from but similarly separated from that end by those sets of corresponding turns which are nearer that end. The turns of each set form an angle to one another which increases from an acute angle for the first set to an increasingly more obtuse angle as the distance of the set from that end increases, to a maximum of 180° at a desired number of sets of corresponding turns from that end. Preferably, the corresponding turns in the first set are substantially parallel to each other. Preferably, corresponding turns of sets at each end of the inductor are flared towards one another in this way.

In the embodiment shown in FIGS. 4*d* and 4*e* (described further below), Litz wire is used as the conductor. It has been found, with regard to the coil ends, that satisfactory results can be obtained in this embodiment with but one set of corresponding turns at each end, the turns in each set being at a very acute angle to one another (for example substantially parallel). For complete elimination of leakage fields, two or more sets of corresponding turns may be preferred.

The transformer of FIG. 4*a*, as stated above, can be employed to transfer very high power levels. Of course, when significant power levels are transferred, the primaries carry high current densities, especially at higher frequencies where the well known ‘skin effect’ confines the current to the surface layers of the conductor and therefore increases the effective resistance of the primary circuit, which may cause excessive and undesirable heating of the primary during operation. To overcome this undesirable increase in resistance, the primary may be composed, as depicted in FIGS. 4*b* and 4*c*, for example, of several “figure-of-eight” or “D” shaped structures, segments 100, 101, 102, 103, 104, 105, 106, 107, 108, 109, 110 and 111, which are secured or laminated together, for example, by bolts, rivets, solder joints or welds, to be electrically in parallel and to have good electrical contact at the bottom and top of the figure of eight or, in the case of the D shaped structures, in the middle of the curved segments of the ‘D’s 113 or at one end of the arcuate segments 112 and 114 (the latter shown in dashed outline); but separated or splayed out in those regions between the loops or D’s, for example, by dielectric inserts, between the individual layers 115, 116, 117, 118, 119 and 120 of the structure, of strips of an insulating dielectric 121, 122, 123 and 124. In similar fashion, the terminations of such coils may be affixed separately to the bus-bar which serves to carry the electrical power to the inductor to increase the surface area of the turns. Because there is no voltage difference between the various segments where they are separated, the dielectric materials used to separate these individual layers may be selected from various polymeric materials.

Again, referring to FIG. 4*a*, it will be apparent that an inductor constructed from laminar shaped turns such as are depicted therein will have a much higher self-capacitance, specifically from the capacitance between successive turns, than would be thought desirable for a high frequency inductor. Normally, in the design of such high frequency inductors, it is customary to minimize self-capacitance to gain the highest Q factor, that is, circuit quality value. However, I have found that it is useful to fabricate the preferred ‘D’ shaped inductor turns with large surface areas for use at AC frequencies in excess of 25 kHz. Unexpectedly, I have discovered that the self-capacitance produced by such large surface area turns has an advantageous effect on the design of circuits employing such inductors, by permitting greater latitude in the design of resonant tank circuits.

Figure 4D:
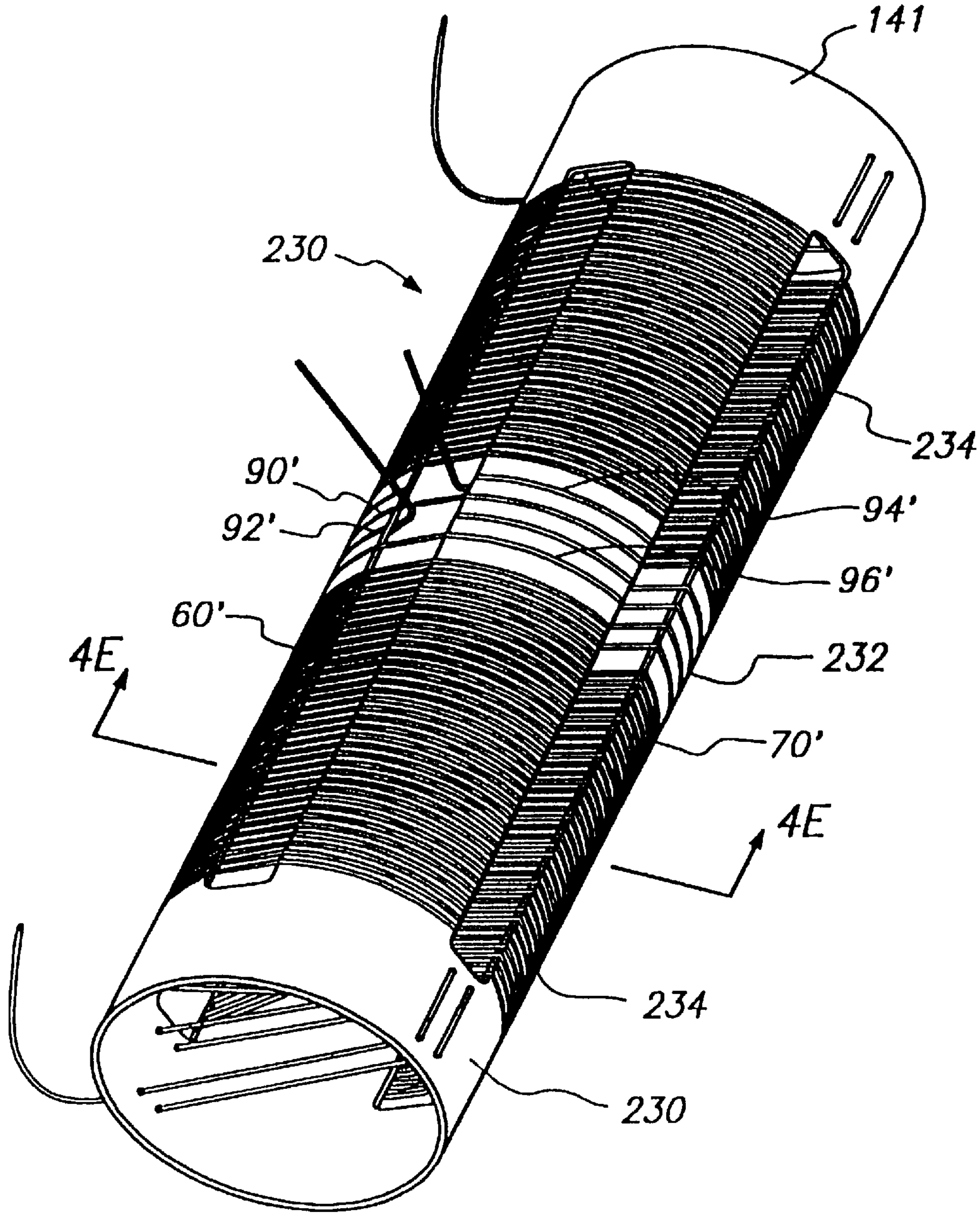
FIGS. 4*d* and 4*e* illustrate another, and preferred, embodiment of the transformer, FIG. 4*e* being a cross-sectional view taken on line 4*e*—4*e* in FIG. 4*d*.
Figure 4E:
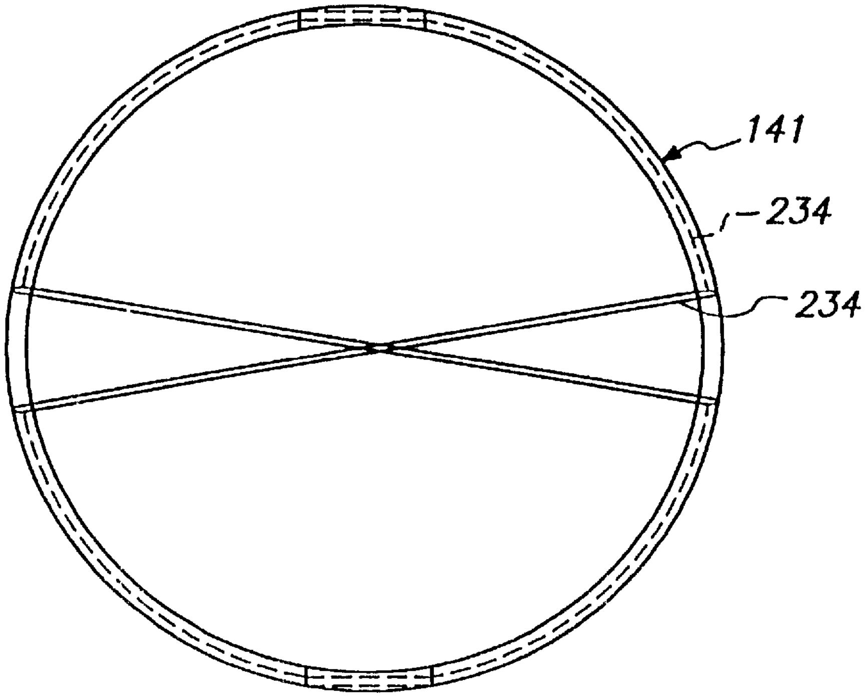

A highly preferred form of transformer 230 is shown in FIGS. 4*d* and 4*e*. As may be seen, primary 232 coils 90',92',94' and 96', and the secondary 234 coils 60', 70', are functionally and electrically equivalent to their unprimed counterparts in FIGS. 4*a*–4*c*. However, in the preferred embodiment of FIGS. 4*d*–4*e*, the conductors are Litz wire wound on a suitably configured frame 141. What is significant, as can be seen in the FIG. 4*e* cross section, is that frame 141 supports the conductors in a pattern which effectively reproduces the ‘D’ shaped coil segment or inductor turn configurations described above. In this embodiment, each sequence as defined above consists of two clockwise or two anticloclkwise turns, thereby enabling a more compact design with very closely spaced turns.

Figure 5A:
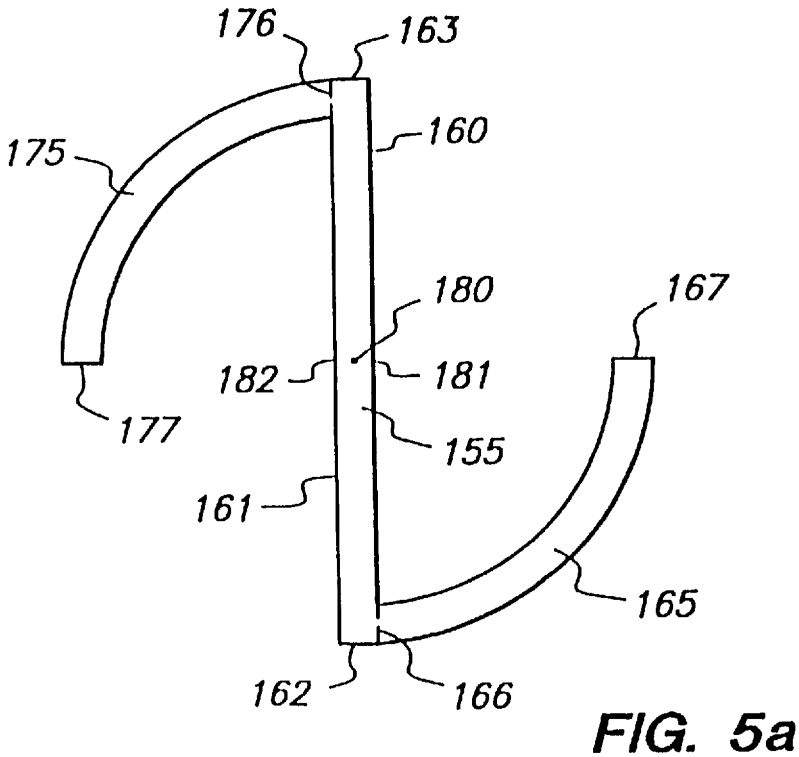
FIG. 5*a* illustrates diagrammatically a preferred embodiment of the laminar inductor element of the invention.
Figure 5B:
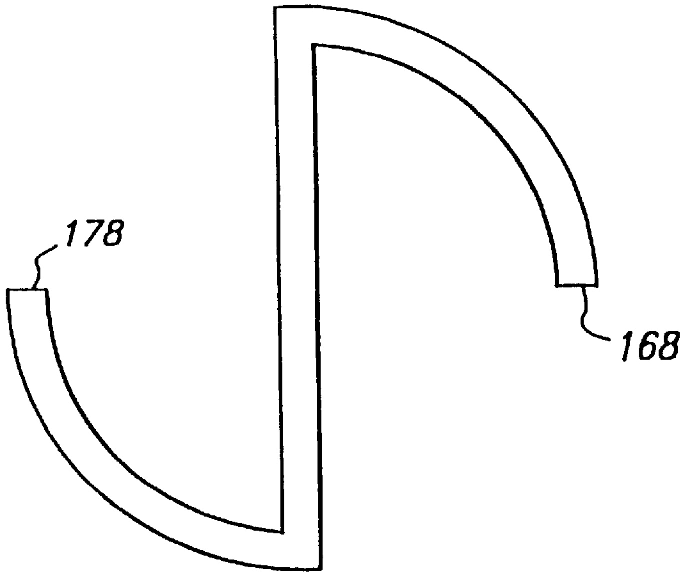
FIG. 5*b* illustrates diagrammatically the FIG. 5*a* preferred embodiment turned over to form a mirror image of FIG. 5*a*.

FIG. 5*a* illustrates diagrammatically one embodiment of the laminar inductor element of the FIGS. 4*a*–4*c* embodiment. The element, which is preferably monolithic, has a first end 167 and a second end 177 and comprises a central rectangular segment with a predetermined length l and width w; a first longitudinal edge 160 and a second longitudinal edge 161. First arcuate segment 165 depends from the first edge and second arcuate segment 175 depends from the second edge. The first arcuate segment and the second arcuate segment are substantially coplanar with the rectangular segment. Each arcuate segment has a width from 0.8 to 5 times that of the rectangular segment, and an outer radius of at least a part of the arcuate segment, taken from a center point, which is from 0.25 to 0.75 times the length of the rectangular segment. The center point 180 lies on the rectangular segment 155, preferably between the first and second edges at about the middle of the rectangular segment, that is between point 181 on first edge 160 and point 182 on second edge 161 but, more preferably, at the center of the rectangular segment. The first arcuate segment 165 has a first end 166 at the first longitudinal edge 160 and at the first end 162 of the rectangular segment, and a second end 167, which is also a first end of the inductor element. The first and second ends of the first arcuate segment subtend at a center point, for example 180, an arc of at least 90°. The second arcuate segment 175 has a first end 176, at the second longitudinal edge 161, and at the second end 163 of the rectangular segment 180, and a second end 177, which is also a second end of the inductor element. The first and second ends of the second arcuate segment subtend at it's center point an arc of at least about 90°. FIG. 5*b* illustrates the mirror image of the laminar inductor element obtained by turning the element of FIG. 5*a* over. The laminate inductor element of FIG. 5*b* has a first end 178 and a second end 168. To form an inductor of the invention, a plurality of the elements of 5*a* and 5*b* are superimposed along the longitudinal dimension of the inductor in alternating and successive sequence on top of each other so that the projections of the central rectangular segment along the longitudinal dimension superimpose. A second end 177 of a FIG. 5*a* element is secured to a first end 178 of the FIG. 5*b* inductor, then the second edge 168 of a superimposed FIG. 5*b* element is secured to a first end 167 of another FIG. 5*a* inductor superimposed on the FIG. 5*b* element. If this alternating and sequential superimposition along the longitudinal dimension of the inductor and securing of alternate ends is carried out, one form of inductor of the invention, such as that illustrated in FIG. 3*a* or 4*a*, is provided. In each one of FIGS. 5*a*, 5*b*, 5*c* and 5*d*, the inductor elements have been depicted in a form optimized for securing elements together by butt welding corresponding ends of mirror image shapes together. If bolting, riveting or soldering is the method of attachment, the arcuate, ‘L’ shaped or substantially linear segments of the elements are made longer, thus subtending angles larger than 90° at the center of the rectangular segments, so that, in assembling mirror image elements together to form inductors of the invention, the first and second ends of mirror image elements are overlapped to facilitate such attachment.

Figure 5C:
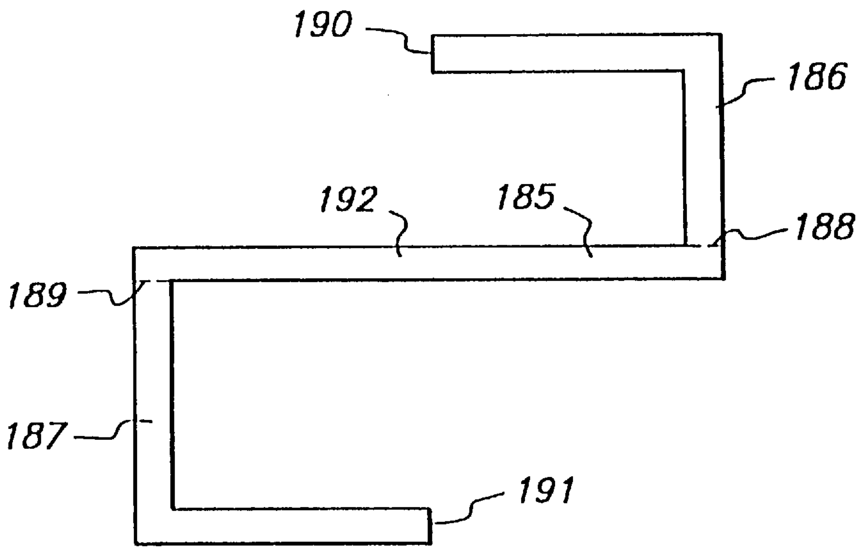
FIGS. 5*c* and 5*d* illustrate diagrammatically other embodiments of the laminar inductor element of the invention.
Figure 5D:
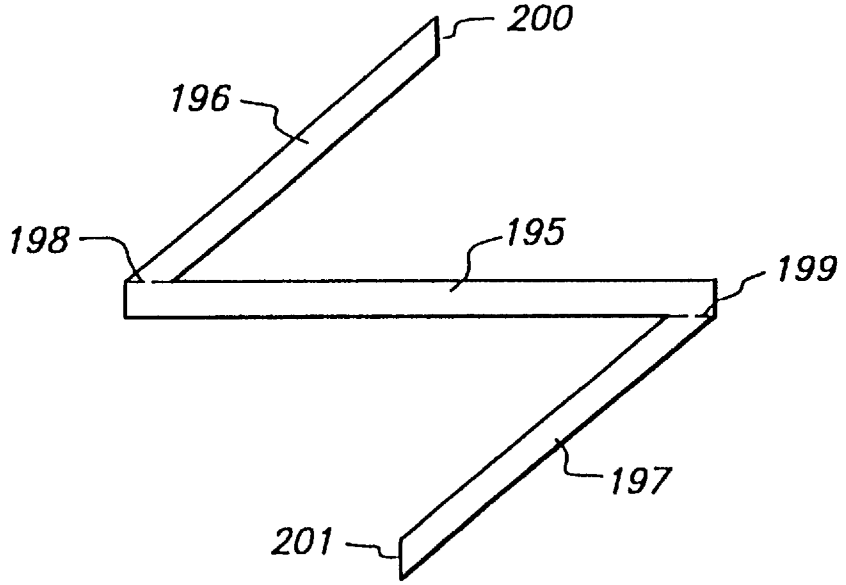

FIGS. 5*c* and 5*d* illustrate other embodiments of the laminar inductor element of the invention, each one, preferably, being monolithic. In FIG. 5*c*, the element has a first end 190 and a second end 191, and the central rectangular segment 185 has depending from it a first ‘L’ shaped segment 186 having a first end 188 secured to one end of one longitudinal edge of the rectangular segment, and a second ‘L’ shaped segment 187 having a first end 189 secured to the opposite end of the other longitudinal edge of the rectangular segment. The first ‘L’ shaped segment has a second end 190, which is also the first end of the element, and the second ‘L’ shaped segment has a second end 191, which is also the second end of the element. The first and second ends of each one of the ‘L’ shaped segments together subtend an angle of at least 90° at the center of the rectangular segment of the element. Similarly, in FIG. 5*d*, the element has a first end 200 and a second end 201, and the central rectangular segment 195 has depending from it a first substantially linear segment 196 having a first end 198 secured to one end of one longitudinal edge of the rectangular segment, and a second substantially linear segment 197 having a first end 199 secured to the opposite end of the other longitudinal edge of the rectangular segment. The first substantially linear segment has a second end 200, which is also the first end of the element and the second substantially linear segment has a second end 201, which is also the second end of the element. The first and second ends of each one of the substantially linear segments together subtend an angle of at least 90° at the center of the rectangular segment of the element.

FIG. 6 is a block diagram illustrating the main features of the circuit of the power transfer apparatus of the invention. The circuit supplies AC power to each one of 4 primaries 232 of the loosely coupled transformer 230, although for simplicity only one primary 232 is depicted herein. Electrical (AC) power 229 is supplied via an isolation transformer 240 (here shown as a 3-phase transformer) and a phase angle firing control circuit 245 to a rectifier circuit 250 which preferably comprises silicon controlled rectifiers (or SCR's) and which also contains smoothing and filtering components to provide a continuously variable, for example, 0 to 400 volt DC power supply (for example, up to 250 amps) via connecting link 252 to a series of power MOSFET's, grouped in two banks of eight each for each primary. Again, for simplicity, only two 260 and 262 (one from each bank) are depicted herein. Each MOSFET in the bank represented by MOSFET 260, which for convenience of explanation will be identified as the high side bank (the MOSFET's being called high side MOSFET's), is driven by a high side MOSFET driver 264. Corresponding MOSFET 262 and it's bank are identified as the low side bank and MOSFFT. Each MOSFET 262 in the low side bank is driven by a low side MOSFET driver 266. Each bank of MOSFET drivers is driven by a signal processor 270 arranged so that power pulses are applied to the high side bank of drivers 264 (and through them the MOSFET's) through electrical connection 272 and to the low side bank of drivers 266 (and through them the MOSFET's) through electrical connection 274 in alternating sequence. The signal which the signal processor routes in alternating sequence to the high side bank and the low side bank is supplied to the signal processor through electrical connection 276 by a phase locked loop generator 280 which is controlled to oscillate at a desired frequency by a feedback connection from the secondary 234 of the transformer 230 through electrical connection 236 and capacitor 238. This feedback loop is connected to the phase locked loop generator 280 via electrical connection 282. High voltage regulation is accomplished by feeding a DC signal back from the proportional high voltage divider 242 via connection 243 to the control circuit 245.

The inductance and capacitance of the primary circuit of the transformer 230, which includes the MOSFET's and associated circuitry, are so selected that the primary circuit has a high frequency selectivity (high Q), and its resonance peak lies near to but above the desired oscillation frequency (for example, offset from the secondary resonant frequency so as to match the series tuned circuit impedance to the source driving, impedance). The corresponding parameters of the secondary high voltage circuitry of the transformer are so selected that the secondary circuit manifests a high selectivity and it's resonance peak lies at the desired oscillation frequency (which is slightly affected by the load). Thus the feedback connection between the secondary of the transformer and the phase locked loop generator constrains that generator to generate a square wave at the resonant frequency (usually in excess of 50 kHz, for example at 300 kHz). This square wave voltage signal is fed to the signal processor 270 which converts the square wave into a series of temporally separate pulses which are fed in alternating sequence to the high side MOSFET drivers 264 and to the low side MOSFET drivers 266, and thus to each one of the MOSFET's. Because these pulses are separated in time, the MOSFET's in the high side bank and the MOSFET's in the low side bank never conduct at the same time, so there is no risk of short circuit currents flowing between the banks. The loosely coupled transformer 230, having a high selectivity secondary 234 resonant at the frequency of the pulses, converts these voltage pulses into alternating sine wave power in the secondary circuitry for transmission to a (remote) load. Because the secondary circuit manifests a high selectivity, any disturbance in its circuit, such as may be caused by a voltage transient, a spark or dielectric breakdown, results in an abrupt alteration of the sine wave frequency. This frequency shift is communicated back to the phase locked loop generator 280 via the feedback loop 282, and then communicated via electrical connection 284 through a small DC blocking capacitor 286 connected to a transient detector and fast shut down latching circuit 290 which communicates directly with the MOSFET drivers via electrical connection 292, shutting them down within less than five cycles of the oscillating signal. The frequency shift is also communicated directly to the rectifier control circuit 245 through electrical connections 292 and 294, shutting that down within one lines frequency cycle. Thus this circuit is very well protected against transients and will shut down so quickly that little or no damage is caused by such transients. In a preferred embodiment, the terminals of the secondary of the transformer 230 are connected to electrodes (see 520,530) of a voltage multiplier, more preferably, of the invention.

Figure 7:
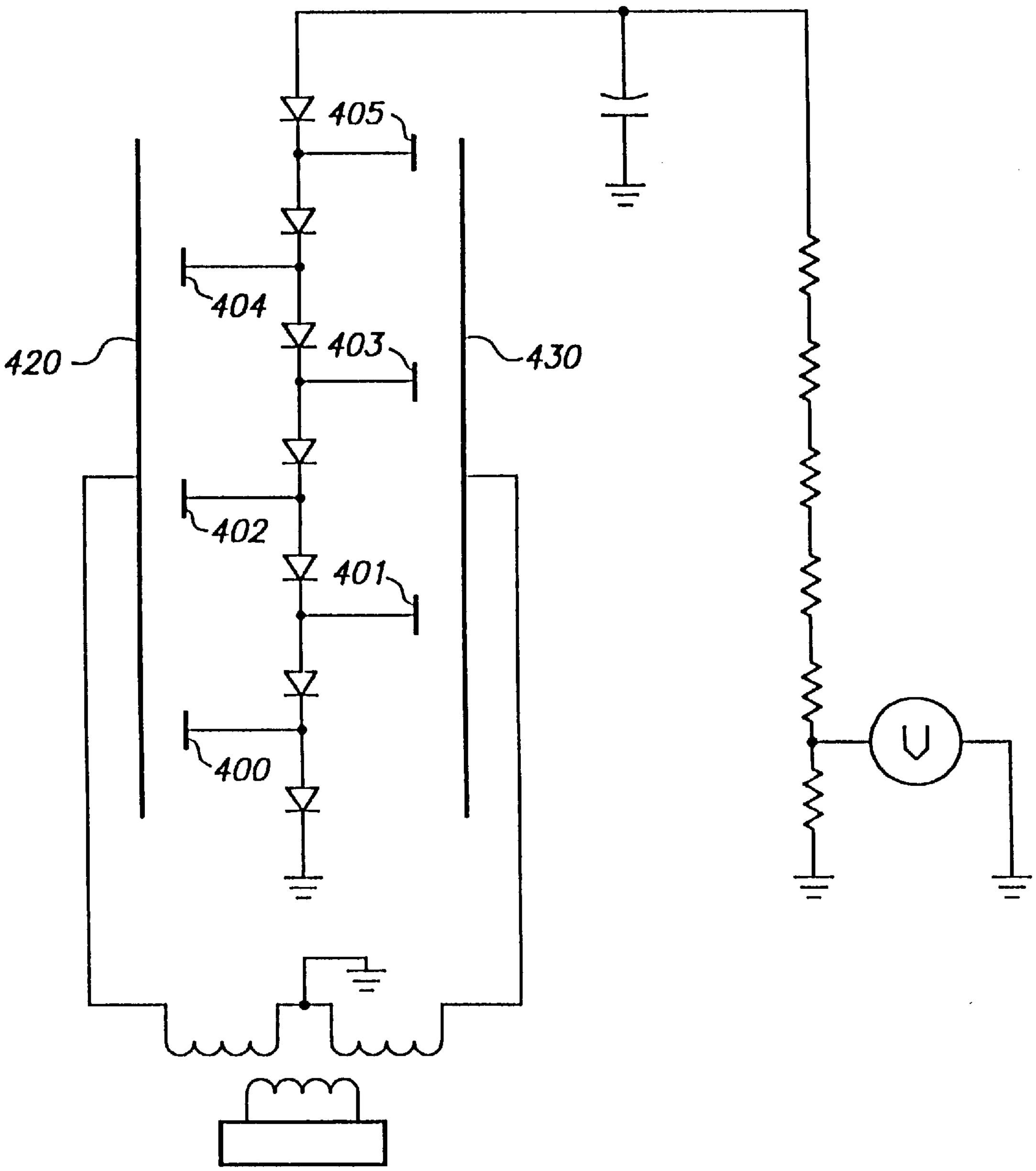
FIG. 7 PRIOR ART
FIG. 7, which is not an example of the invention, illustrates diagrammatically a voltage multiplier of the prior art.
Figure 8:
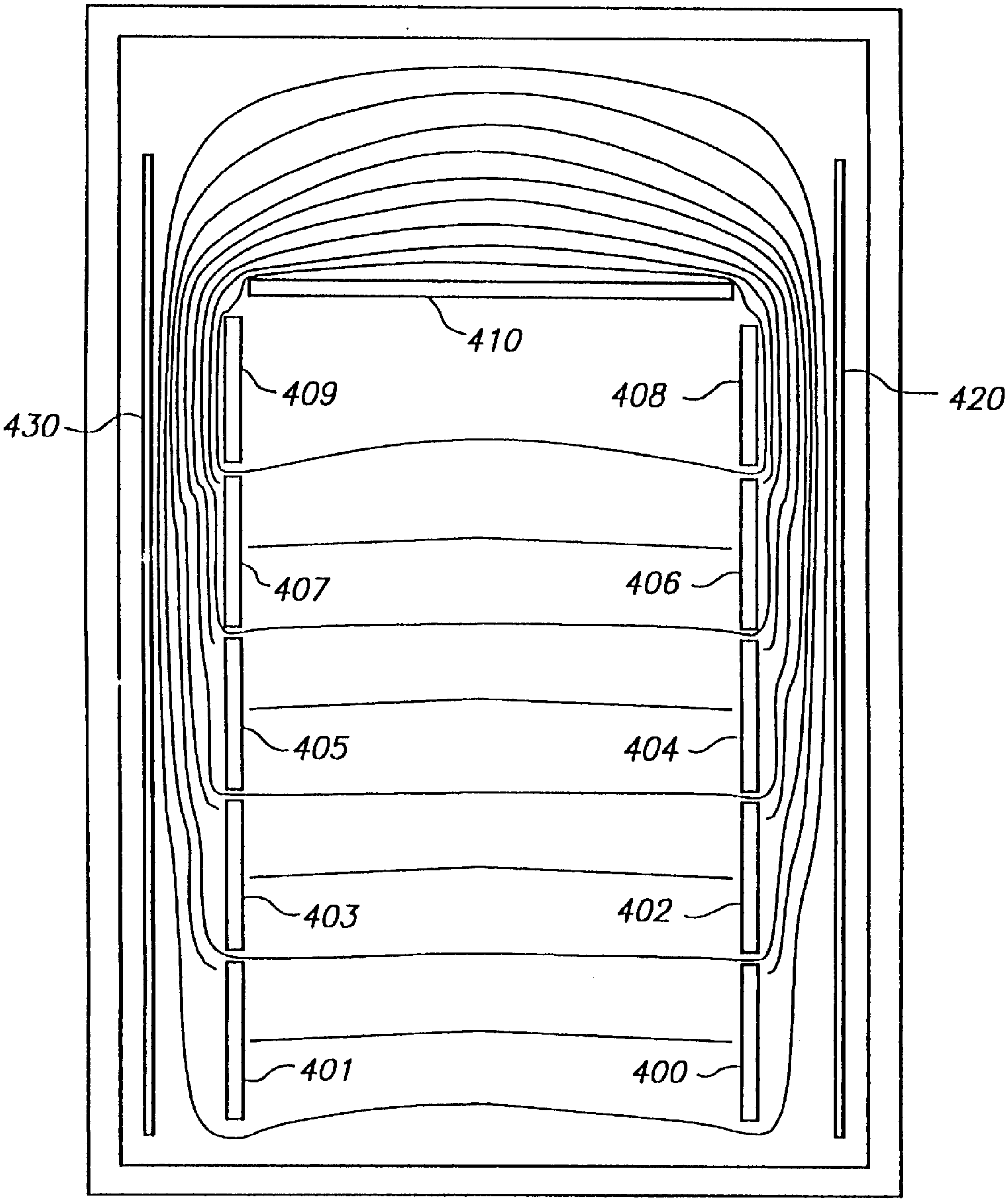
FIG. 8 PRIOR ART
FIG. 8 illustrates a computed model of the equipotential field lines in successive capacitors of such a voltage multiplier of the prior art.

FIG. 7, which is not an example of the invention, illustrates in two dimensions a parallel fed voltage multiplier of the prior art, wherein all the cascade capacitor plates 400, 401, 402, 403, 404, are at the same distance from one or the other feed electrode 420 or 430. See, for example, U.S. Pat. Nos. 3,246,230, and 3,063,000. FIG. 8 is a computer generated representation of the voltage gradients in such a prior art voltage multiplier. Because, in such a system, the distance separating the plates of each capacitor is determined by the maximum design voltage gradient in the highest voltage capacitors 408–430 and 409–420, lower voltage capacitors operate at lower and lower voltage stresses as the applied voltage drops. The applied voltage increases in equal steps from one capacitor plate to the next for the sequence 400, 402, 404, 406 and 408 and for the sequence 401, 403, 405, 407 and 409. In commercial voltage multipliers of this type the voltage also increases in equal steps between 400 and 401, 401 and 402, 402 and 403, and so on. This complication is simplified herein to facilitate understanding of the figure. Treating these capacitors as parallel plate capacitors, the capacitance C=k times A/D where k is a proportionality constant, A is the area of the cascade plates and D is the distance apart of the plates from their feed electrodes. Thus the required area A (for a plate of a capacitor)=C times D/k. For a parallel fed cascade high voltage multiplier, all capacitances are preferably equal, so that A for any capacitor=K times D. Thus, for n capacitors, the total capacitor area required $A_t$=K times the sum from 1 to n of the individual capacitor areas, D. With the structure shown in FIG. 7, D is a constant so the total capacitor area is K times n times D and it is this value which sets the size of the multiplier array.

Figure 9:
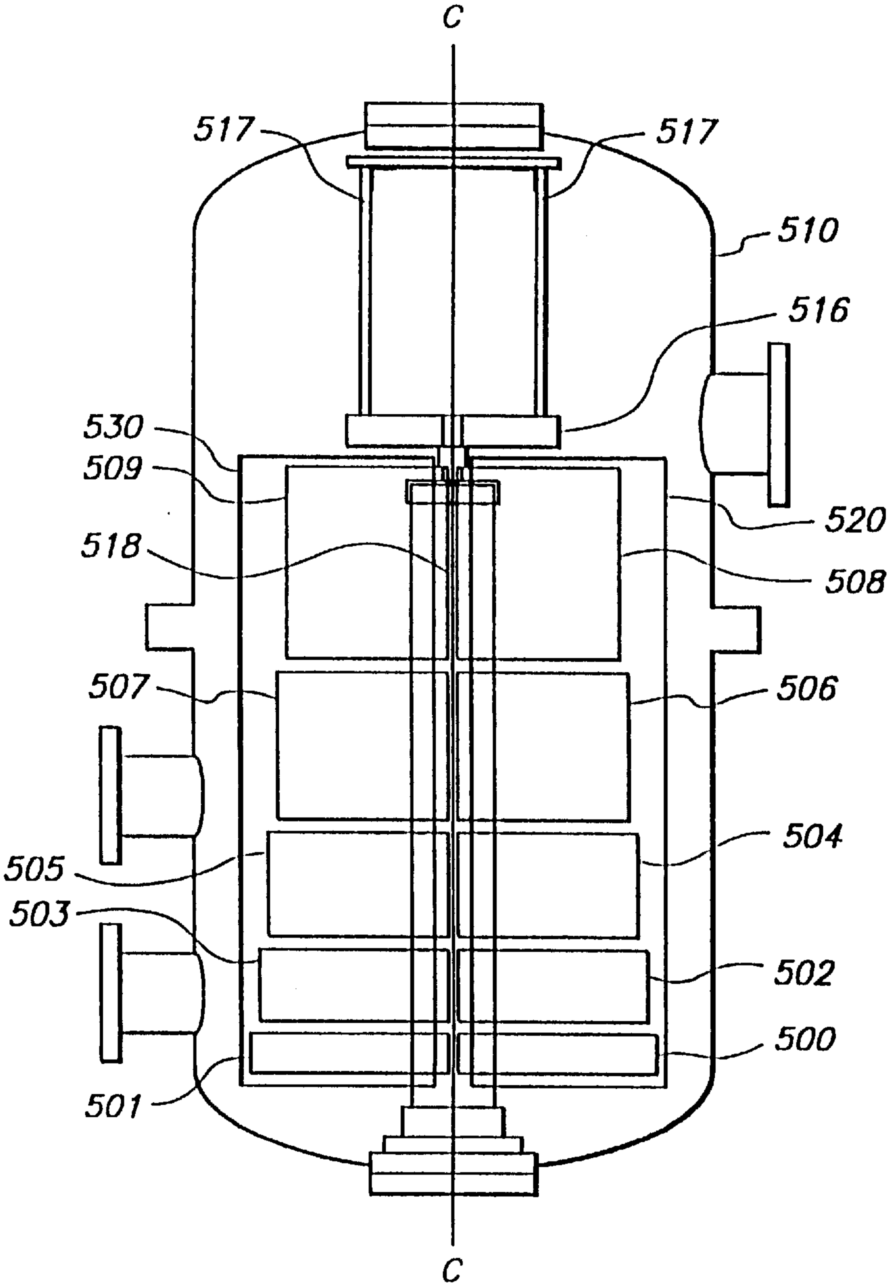
FIG. 9 illustrates diagrammatically an embodiment of the voltage multiplier of the invention showing the capacitor configuration.
Figure 10:
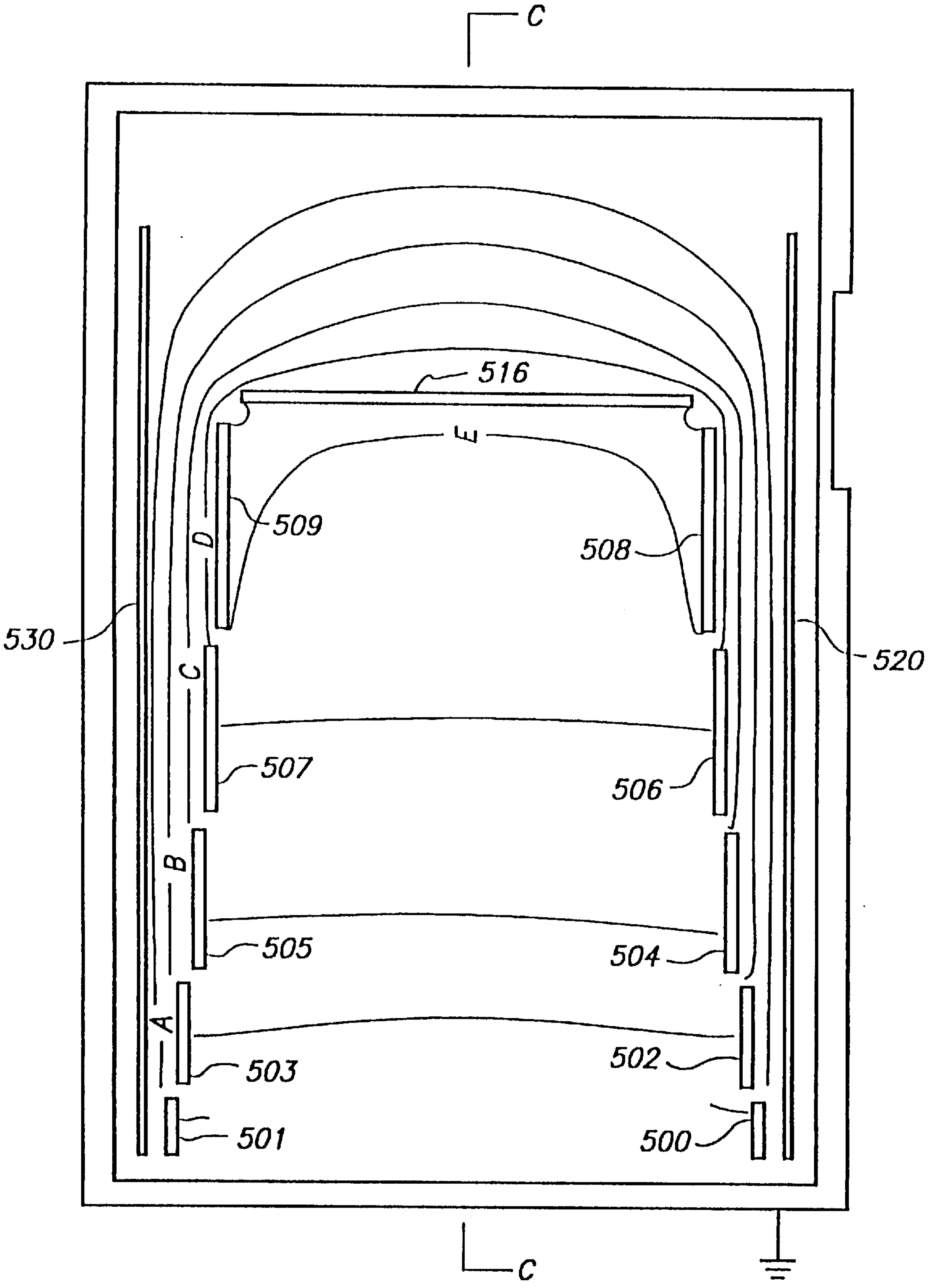
FIG. 10 illustrates a computed model of the equipotential field lines in successive capacitors of the FIG. 9 embodiment of the voltage multiplier of the invention.

FIG. 9 illustrates a voltage multiplier according to the present invention. A computer generated representation of the voltage gradients in such a configuration is shown in FIG. 10. The main feed electrodes 520, 530, which are electrically connected to and receive the output from an AC power source, preferably the transformer secondary 234 of FIG. 6, feed or energize a stack of capacitor plates 500, 501, 502, 503, 504 . . . 509, which are arrayed along a longitudinal dimension c . . . c of the voltage multiplier, and which are placed at connections between cascaded rectifiers (not shown). Because, in this design, the distances between the capacitor plates and the adjacent electrode are varied to maintain the DC voltage gradients approximately constant from one capacitor plate to the next higher in the stack, the plates are not required to have the same area to manifest the same capacitance. In the preferred embodiment of this aspect of the invention, the distances between successive capacitor plates in the cascade increase in substantially equal increments so that a substantially constant DC field gradient is maintained between all the plates and adjacent feed electrodes. FIG. 10 illustrates the substantial uniformity of the field obtained by such an arrangement, where the identifying numbers correspond exactly to those of FIG. 9. Because the DC field gradients are substantially uniform, there are no high stress regions, which considerably simplifies the design requirements for the capacitor plates. It has been found that, unlike prior art configurations, only minimal smoothing of the edges is required and no special shaping, smoothing, curving or polishing of the capacitor plates is needed to prevent unwanted discharges. In addition, because lower voltage capacitor plates are positioned closer to the adjacent electrode, the corresponding plate areas are reduced such that in the preferred configuration as discussed above, the average distance between a capacitor plate and the adjacent electrode now becomes D/2 so that the total area is given by K times n times D/2, and a voltage multiplier of the invention can be placed in a housing only half of the volume required to house equivalent capacitance prior art voltage multipliers. FIG. 9 also shows high voltage terminal 516 and its insulating support 517.

Figure 11:
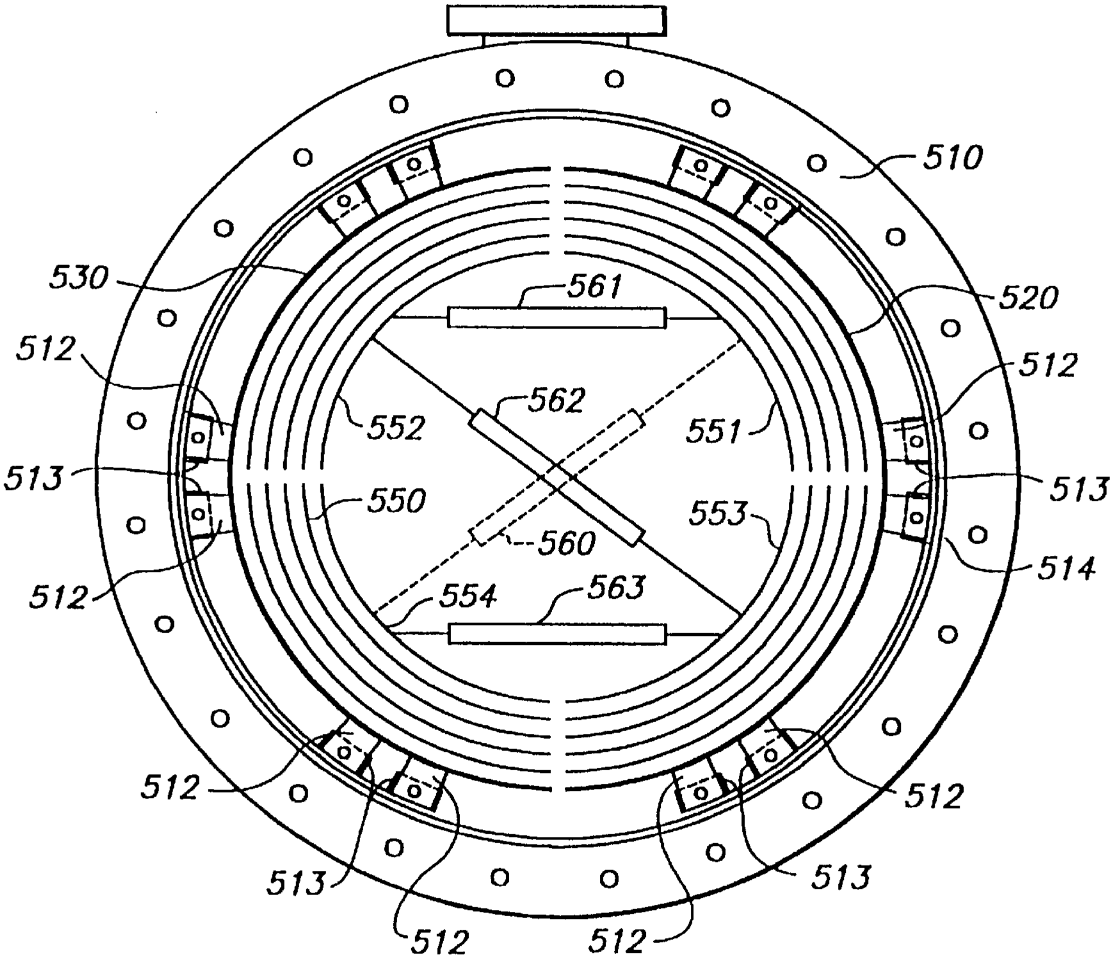
FIG. 11 illustrates diagrammatically details of a preferred embodiment of the voltage multiplier of the invention laid out as four capacitor quadrants per module and configured for use in an apparatus for irradiating a substrate.

FIG. 11 illustrates in cross section a preferred embodiment of the voltage multiplier of FIG. 9, in which the metallic electrodes 520 and 530, adapted to be connected to a source of AC power such as the terminals of the transformer secondary 234 of FIG. 6, are spaced apart and formed into semi-cylindrical surfaces elongated along a common axis (c . . . c as depicted in FIG. 9). In this embodiment the voltage multiplier is positioned within a gas tight container, for example a pressure vessel 510, as shown in FIG. 9. Each one of the electrodes is secured to a plurality of insulating dielectric spacers 512, positioned within retaining supports 513, which are secured to the container wall 514. The voltage multiplier also comprises a plurality of solid state rectifier units, each having an anode and cathode, which are positioned between the electrodes and are series-connected, positive to negative terminal, between ground and a high voltage DC terminal 516 (not shown in FIG. 11). For simplicity, only the top four rectifier units 560, 561, 562 and 563 are shown. A capacitor plate is connected to each one of the electrical junctions thereby formed between the rectifier units. Each capacitor plate is formed into a quadrant of a cylindrical surface, for example, 550 of FIG. 11 and, in combination with one of the electrodes 520 or 530, forms a capacitor having a predetermined capacitance, the capacitor plate and the electrode being spaced a predetermined distance apart. Each quartet of quadrants, for example 551, 552, 553 and 554 forms a cylindrical module in which each capacitor plate is positioned at substantially the same distance apart from the nearest electrode to that capacitor plate. Thus, successive quartets of quadrants form a plurality of said modules serially arranged along the elongated dimension of the two electrodes 520 and 530. In this embodiment, as can be seen, the spacing between each capacitor plate of successive modules, serially disposed between the ground terminal and the high voltage DC terminal, and the nearest electrode increases in substantially equal steps. The capacitor plates serve to capacitively couple an AC potential of substantially equal amplitude across the capacitors via the capacitance between the capacitor plates and the adjacent electrode. The capacitance between a capacitor plate and an electrode in this embodiment is substantially identical to an average value of capacitance between the capacitor plates and electrodes. Using the topmost module of this figure, for the sake of clarity, as a first module, a first capacitor quadrant 551 in this module is series connected via a first rectifier unit 560 to another component and to a neighboring second capacitor quadrant 552 in the first module via a second rectifier unit 561. (Unit 560 is shown dotted to indicate that the component it is connected to is either electrical ground—this would be the case if this module was the bottom module—or an opposed capacitor quadrant 550 in a neighboring second module, just below the topmost module of FIG. 11.) The second capacitor quadrant 552 in the first module is also connected via a third rectifier unit 562 to an opposed third capacitor quadrant 553 in the first module; the third capacitor quadrant plate 553 in the first module is also connected via a fourth rectifier unit 563 to a neighboring fourth capacitor quadrant plate 554 in the first module; and the fourth capacitor quadrant plate is also connected via a fifth rectifier unit (not shown) either to the high voltage DC terminal if it is the topmost module (as in this instance) or, if the module is situated lower down in the capacitor stack, to an opposed capacitor quadrant plate in a neighboring third module.

Figure 12:
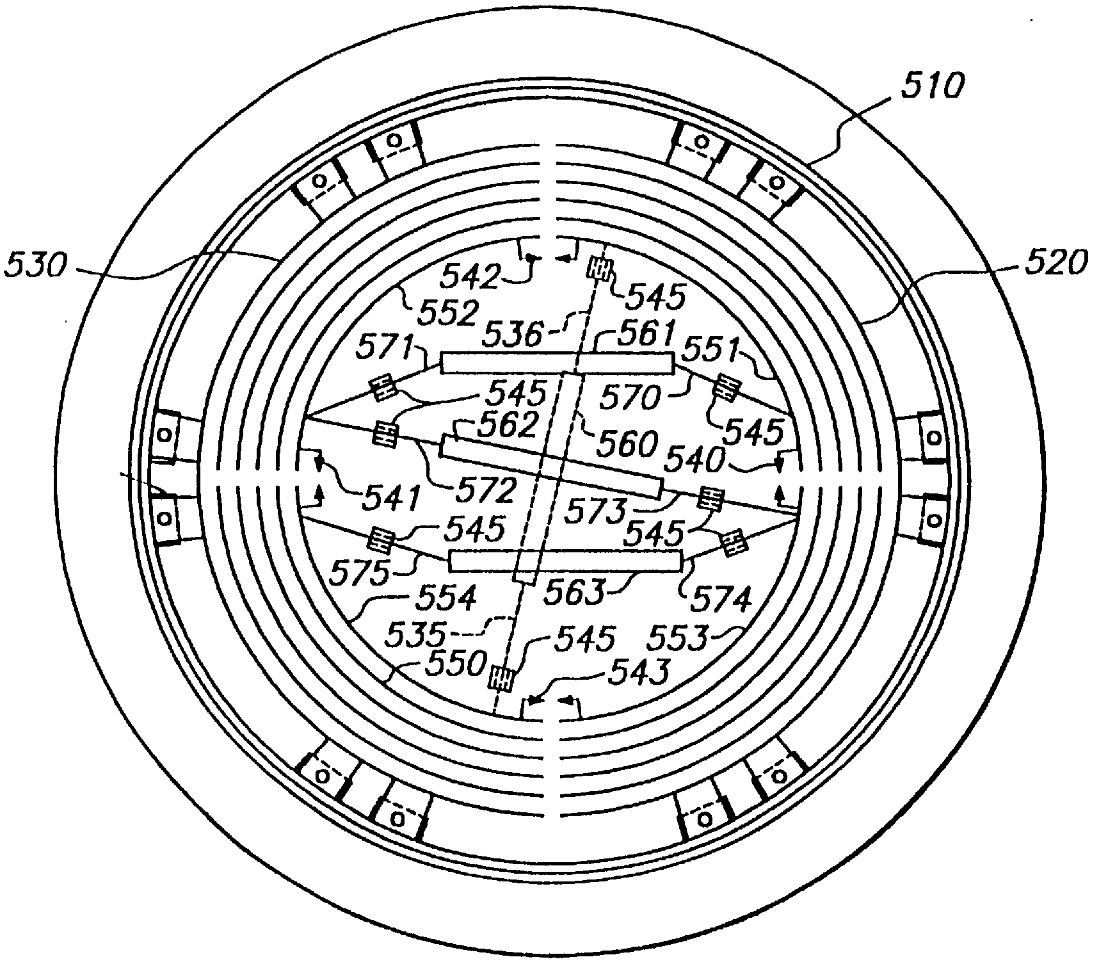
FIG. 12 depicts diagrammatically an embodiment of the voltage multiplier of the invention laid out as four capacitor quadrants per module illustrating details of the spark gaps and ferrite bead protection means used between successive quadrants of the voltage multiplier.
Figure 12A:
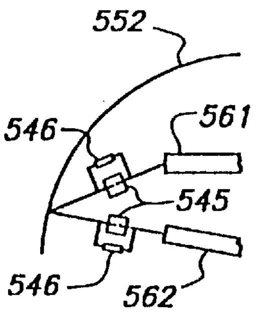
FIG. 12*a* illustrates optional shunt resistors around the ferrite beads.

FIG. 12 illustrates in cross section a protective system for protecting the rectifier units of a voltage multiplier, particularly those of the invention. The pressure vessel 510 has positioned within it the two metallic electrodes 520 and 530, adapted to be connected to a source of AC power, which are spaced apart and formed into semi-cylindrical surfaces elongated along a common axis. As also previously described, a plurality of solid state rectifier units, each having an anode and cathode, is positioned between the electrodes and series-connected, positive to negative terminal, between ground and a high voltage DC terminal (not shown in FIG. 12). For simplicity, only the top four rectifier units 560, 561, 562 and 563 are shown, and they are connected together and disposed exactly as described for FIG. 11. One of the capacitor plates 550, 551, 552, 553 and 554 is connected at each one of the electrical junctions thereby formed between the rectifier units. Spark gaps 540, 541,542 and 543 are placed at facing edges of capacitor plates 551 and 553, 552 and 554, 551 and 552, and 553 and 554. Rectifier units 560, 561, 562 and 563 are each connected between capacitor plates 550 and 551, 551 and 552, 552 and 553, and 553 and 554 respectively via electrical connection 535 and 536, 570 and 571, 572 and 573, and 574 and 575, each of which comprises means 545 for dissipating electrical transients, which are preferably ferrite high frequency attenuator beads having a central aperture through which the electrical connection is threaded. The beads may be shunted by a small resistance 546 (e.g., 1000 Ω) (FIG. 12*a*), if helpful to suppress corona around the beads. It has been found that connecting these electrical connections to the capacitor plates at positions immediately adjacent to the spark gaps, and placing a means for attenuating and dissipating electrical transients in the connection adjacent the position of attachment to a capacitor plate, markedly reduces the risk of voltage transients damaging the rectifier units.

Figure 13:
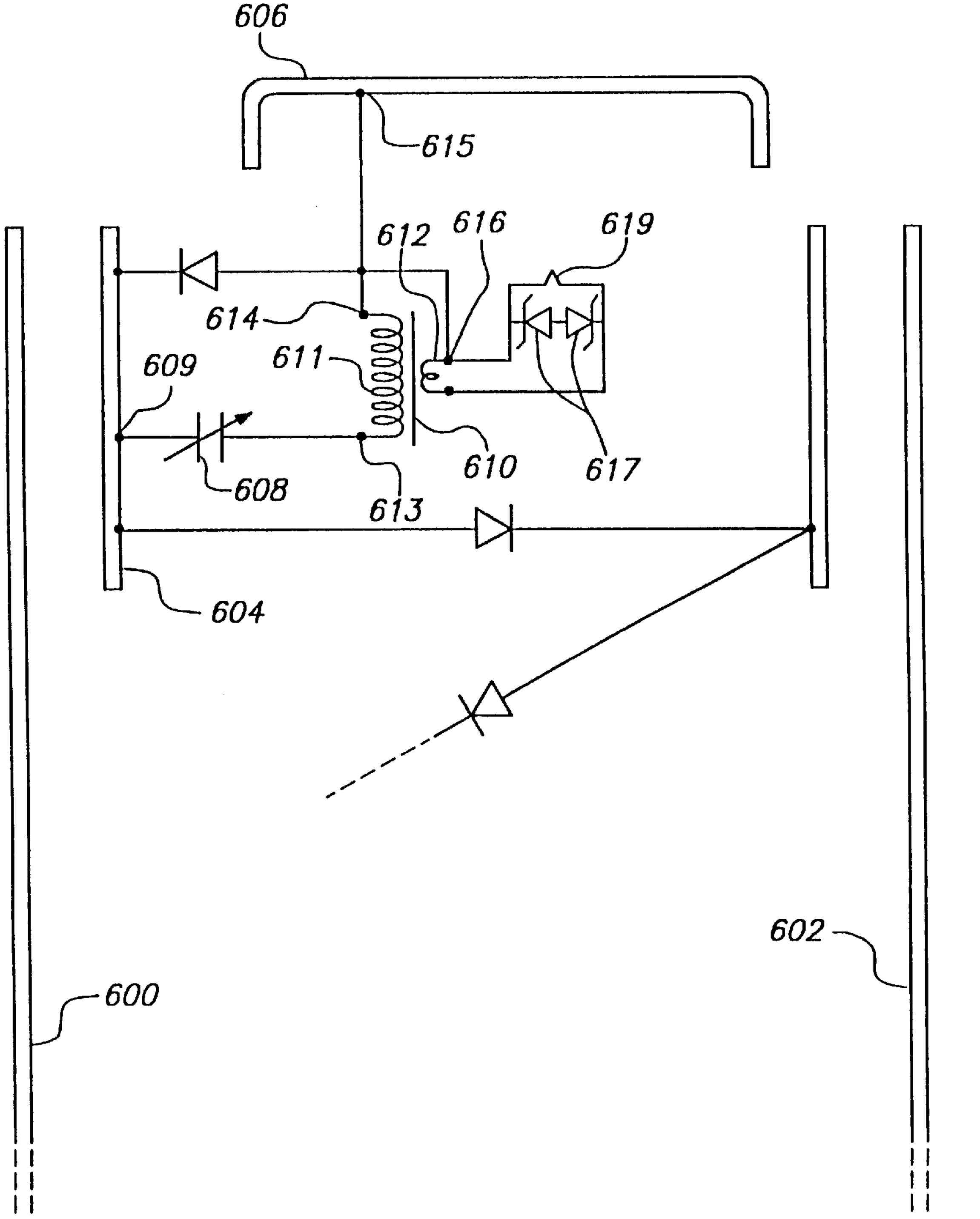
FIG. 13 is a diagrammatic view of an embodiment of the auxiliary power supply of the invention, useful especially in certain embodiments of the voltage multiplier of the invention.

FIG. 13 illustrates diagrammatically an auxiliary power supply, for use with voltage multipliers, which is of particular utility when the voltage multiplier is used in an apparatus for irradiating a substrate. The voltage multiplier may be of any parallel or series fed capacitive type but preferably comprises a pair of metallic electrodes 600 and 602, adapted to be connected to a source of AC power, which are spaced apart and formed into semi-cylindrical surfaces elongated along a common axis. A plurality of solid state rectifier units, each having an anode and cathode, is positioned between the electrodes and is series-connected, positive to negative terminal, between ground and a high voltage DC terminal (as, for example, shown in FIGS. 10, 12 and 13). For simplicity, all details of the electrical connections between the capacitor plates, which have been discussed for the preferred embodiment above, are omitted in FIG. 13. Capacitor plate 604, which is mounted to face electrode 600, and capacitor plate 606 which is the high voltage output terminal of the voltage multiplier (see also FIG. 6) are at different electrical potentials. Between plates 604 and 606 (and thus electrically connected between plates 600 and 606 by virtue of the capacitive coupling between plates 600 and 604) is a variable capacitor 608, connected at 609 to plate 604, and to a terminal 613 of primary 611 of a transformer 610. The other terminal 614 of the primary is connected at 615 to plate 606. High voltage output terminal plate 606 is at DC potential only, because it is centered between the two driver electrodes 600 and 602. One terminal of secondary 612 of the transformer 610 is preferably connected via electrical connections 616 and 615 to plate 606. Preferably, the secondary of the transformer is shunted by two back-to-back Zener diodes 617 to reduce the effect of backwards propagation of any electrical transients such as would occur, for example, if the electrical load on the secondary was interrupted. Such a load night comprise a filament 619 of a particle accelerator (not shown). Variable capacitor 608 provides for controlling the amount of power delivered to load 619.

Figure 14:
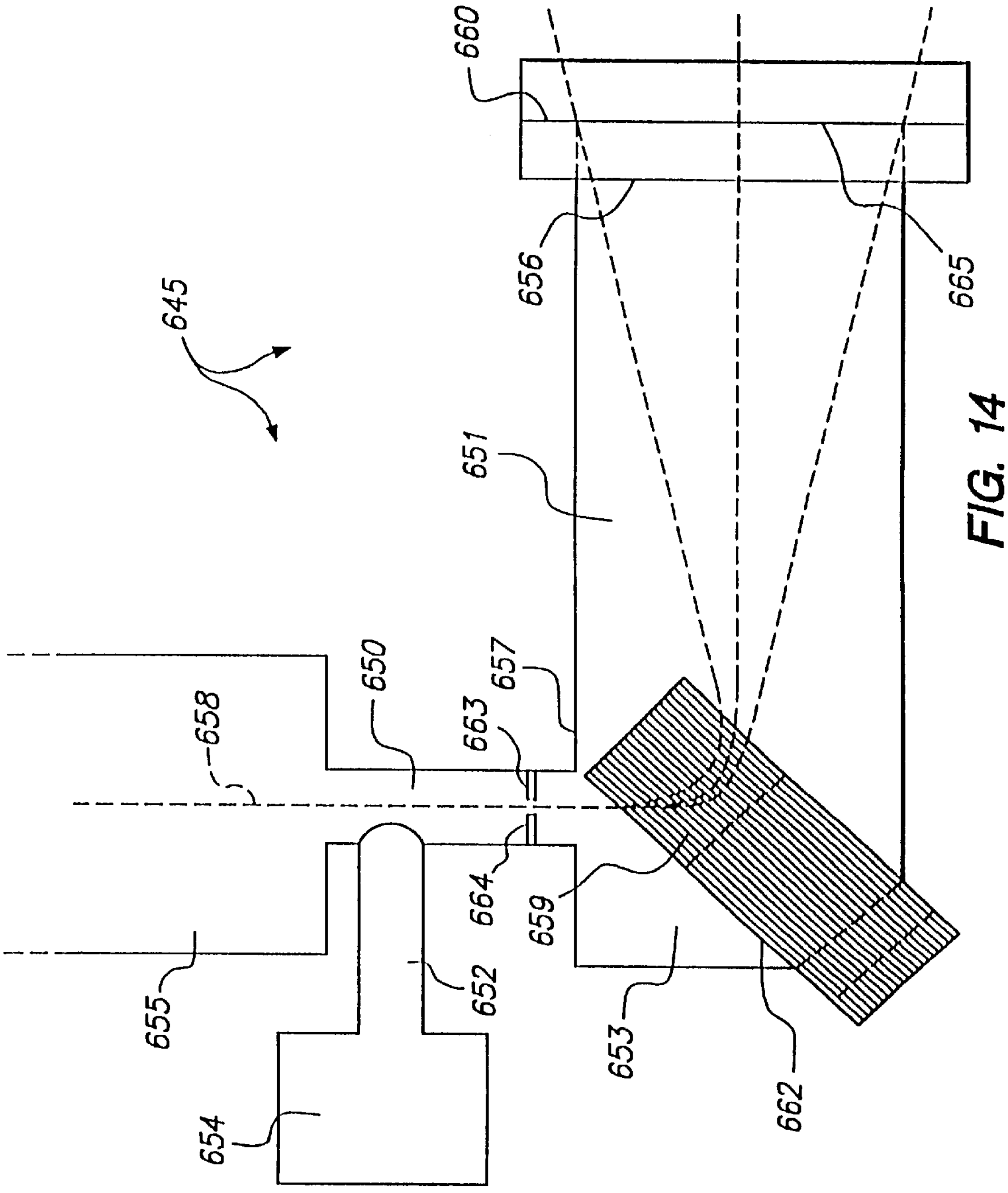
FIG. 14 illustrates diagrammatically an embodiment of the novel drift tube of the invention.
Figure 15:
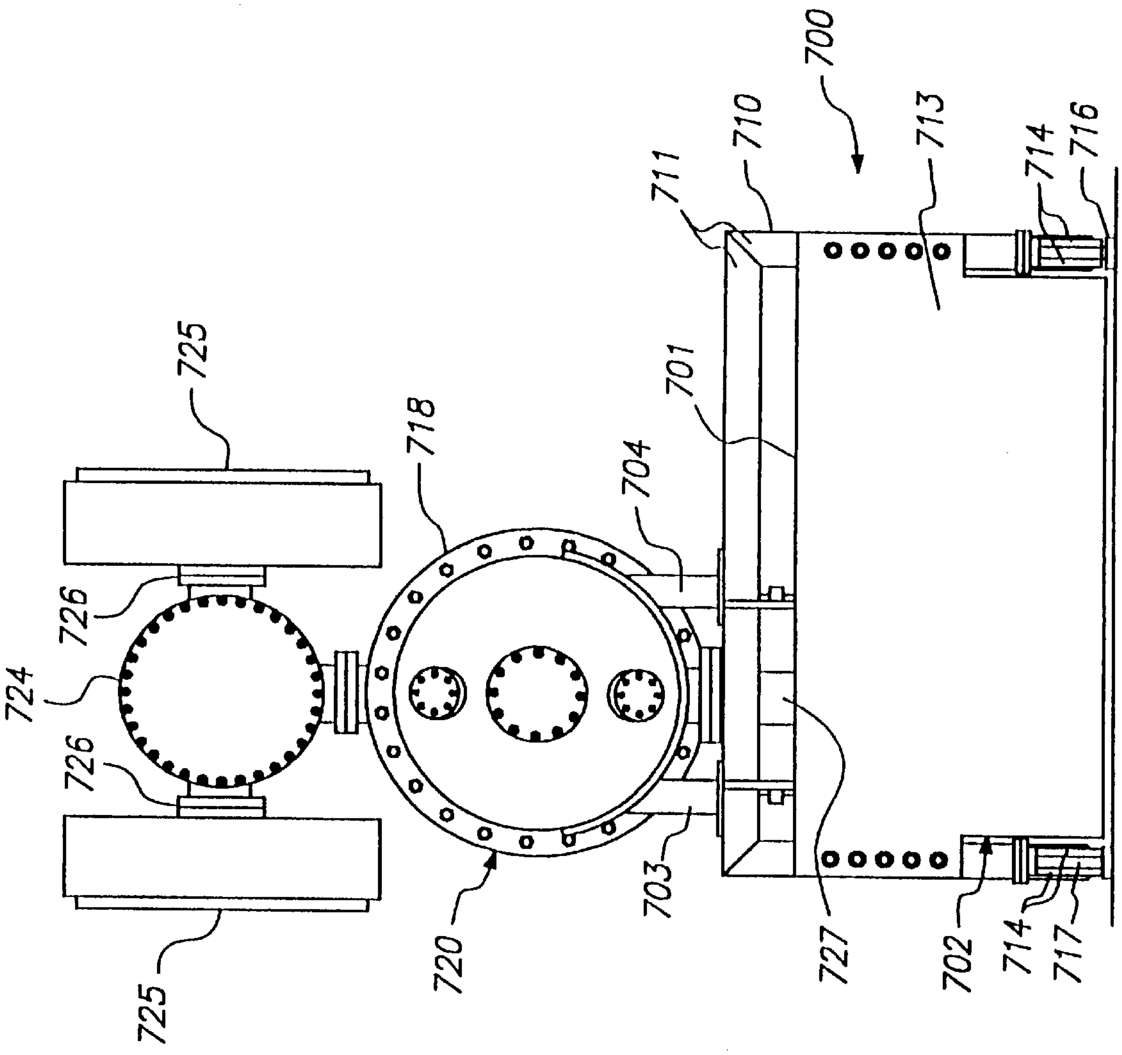
FIG. 15 illustrates schematically a frontal view of an embodiment of the compact self shielded apparatus for irradiating a substrate.
Figure 16:
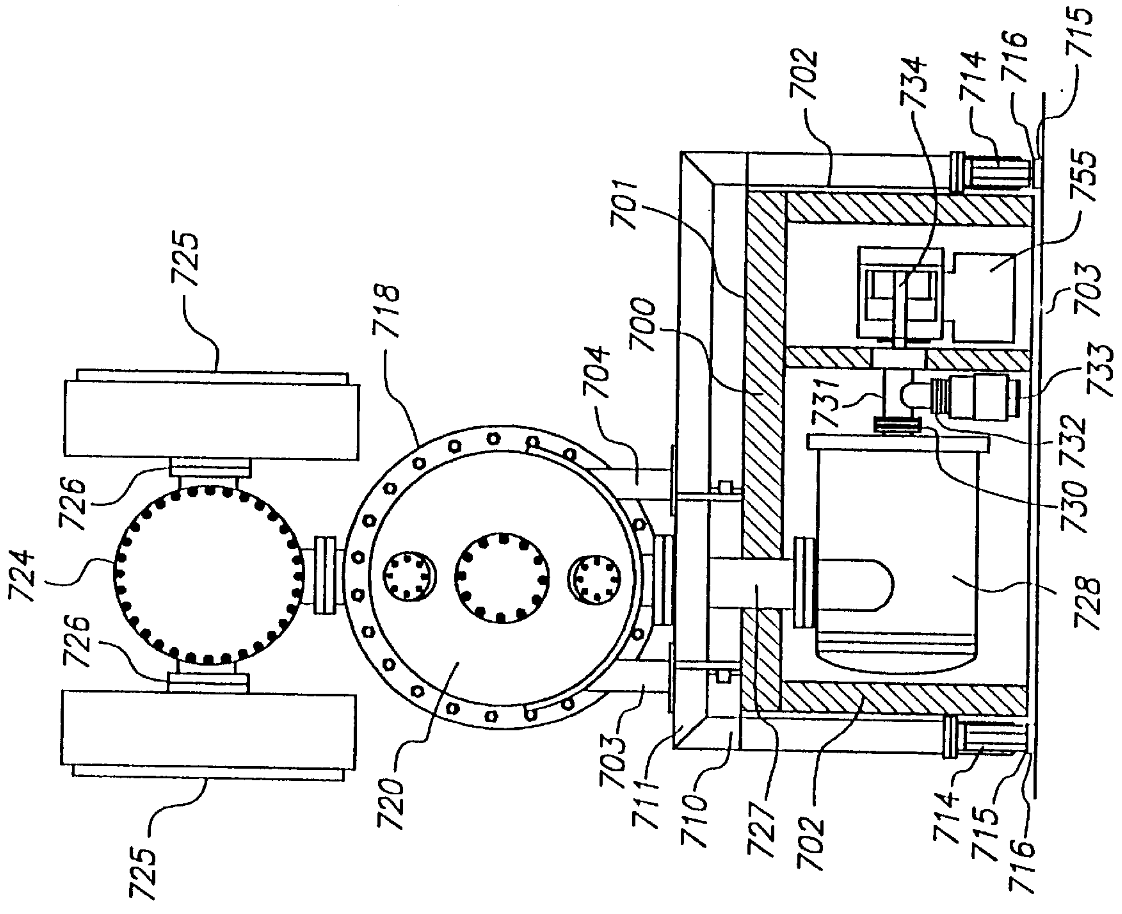
FIG. 16 illustrates the FIG. 15 structure with the front shield wall removed to better show the component arrangement therewithin.
Figure 17:
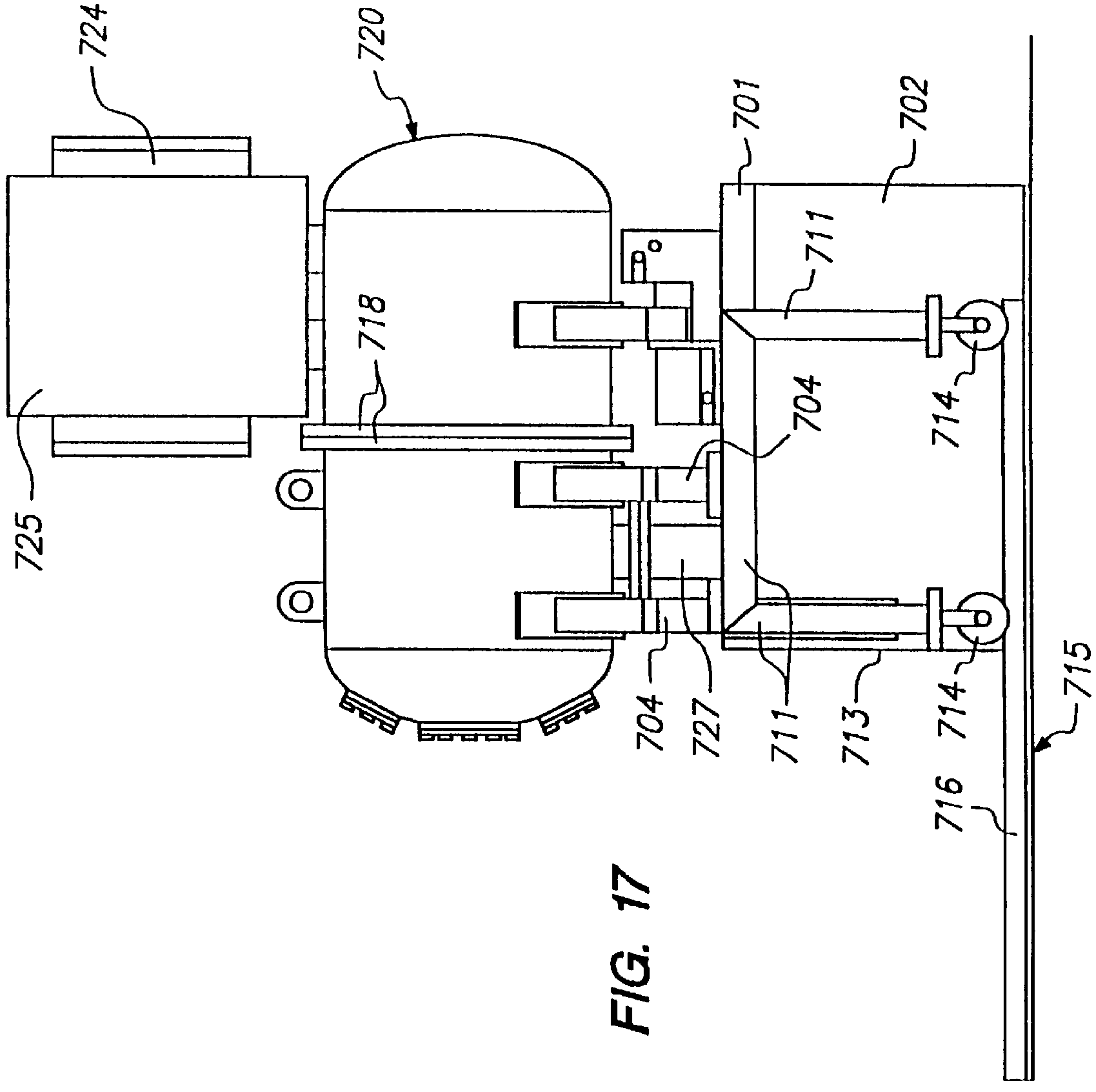
FIG. 17 is a side view of the FIG. 15 embodiment.
Figure 18:
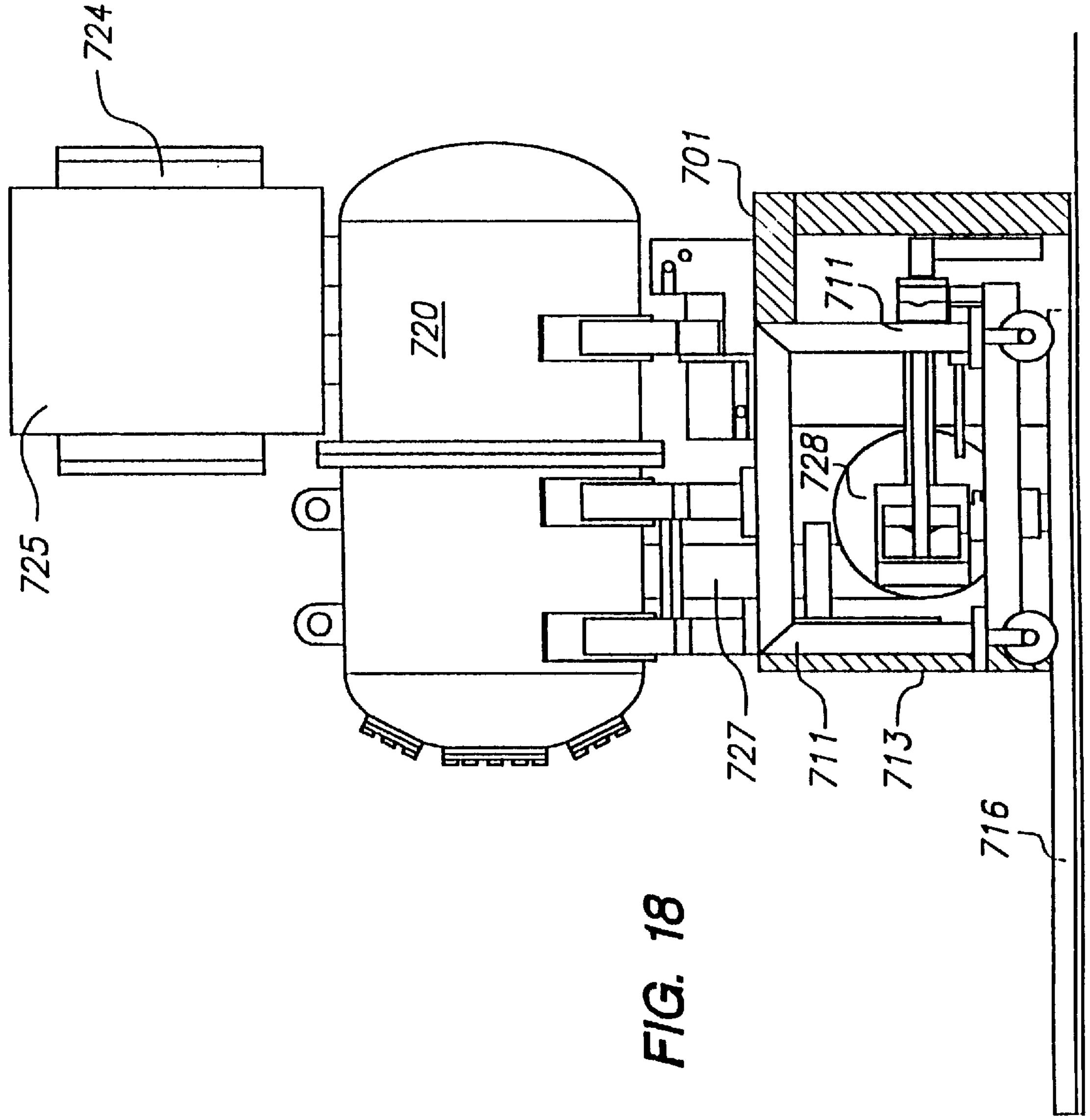
FIG. 18 illustrates the FIG. 17 embodiment with the nearer side shield wall removed to better show the component arrangement therewithin.
Figure 19:
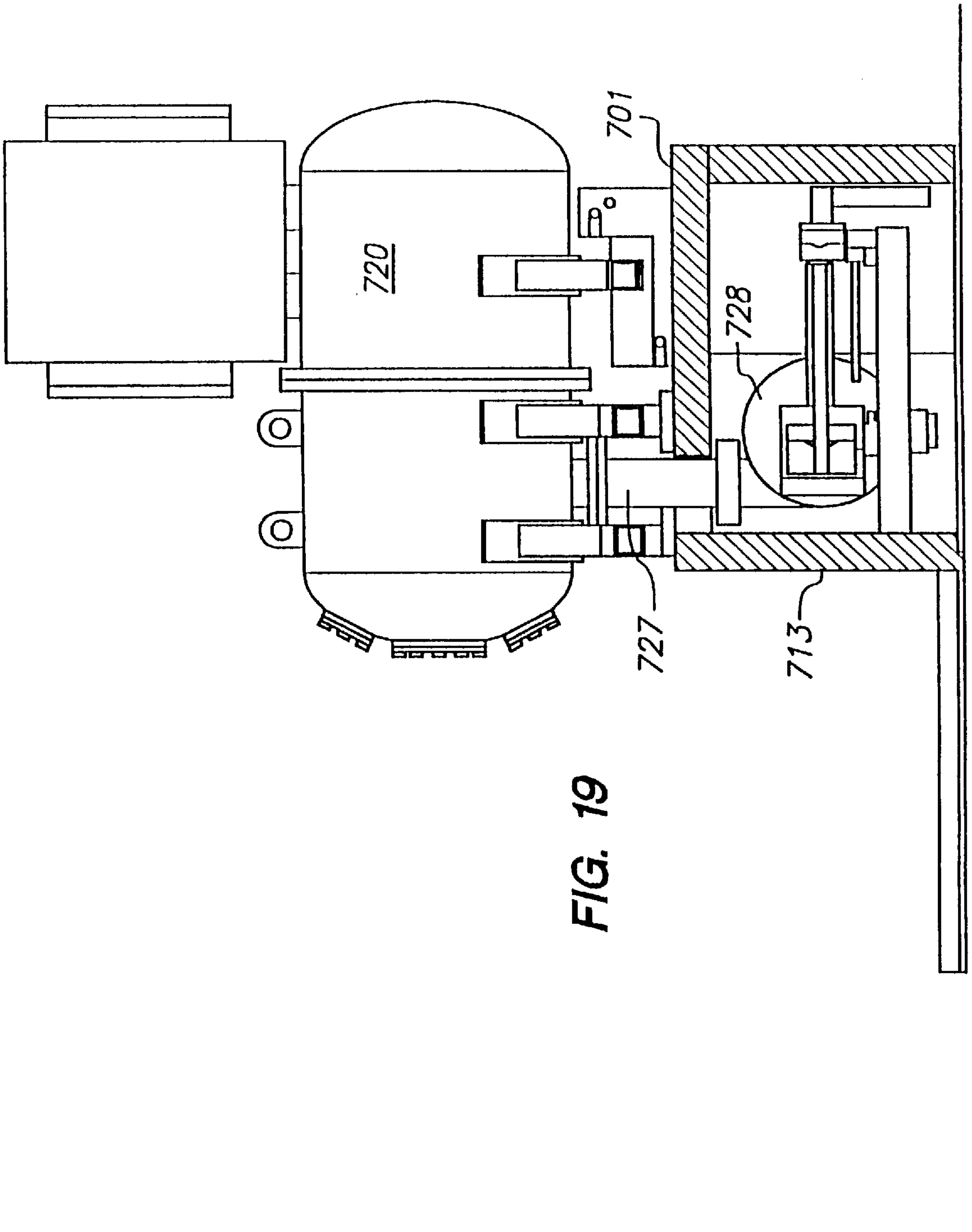
FIG. 19 is a partial cross-sectional side view of the embodiment of FIGS. 15–22 taken generally on line 19—19 in FIG. 20.
Figure 20:
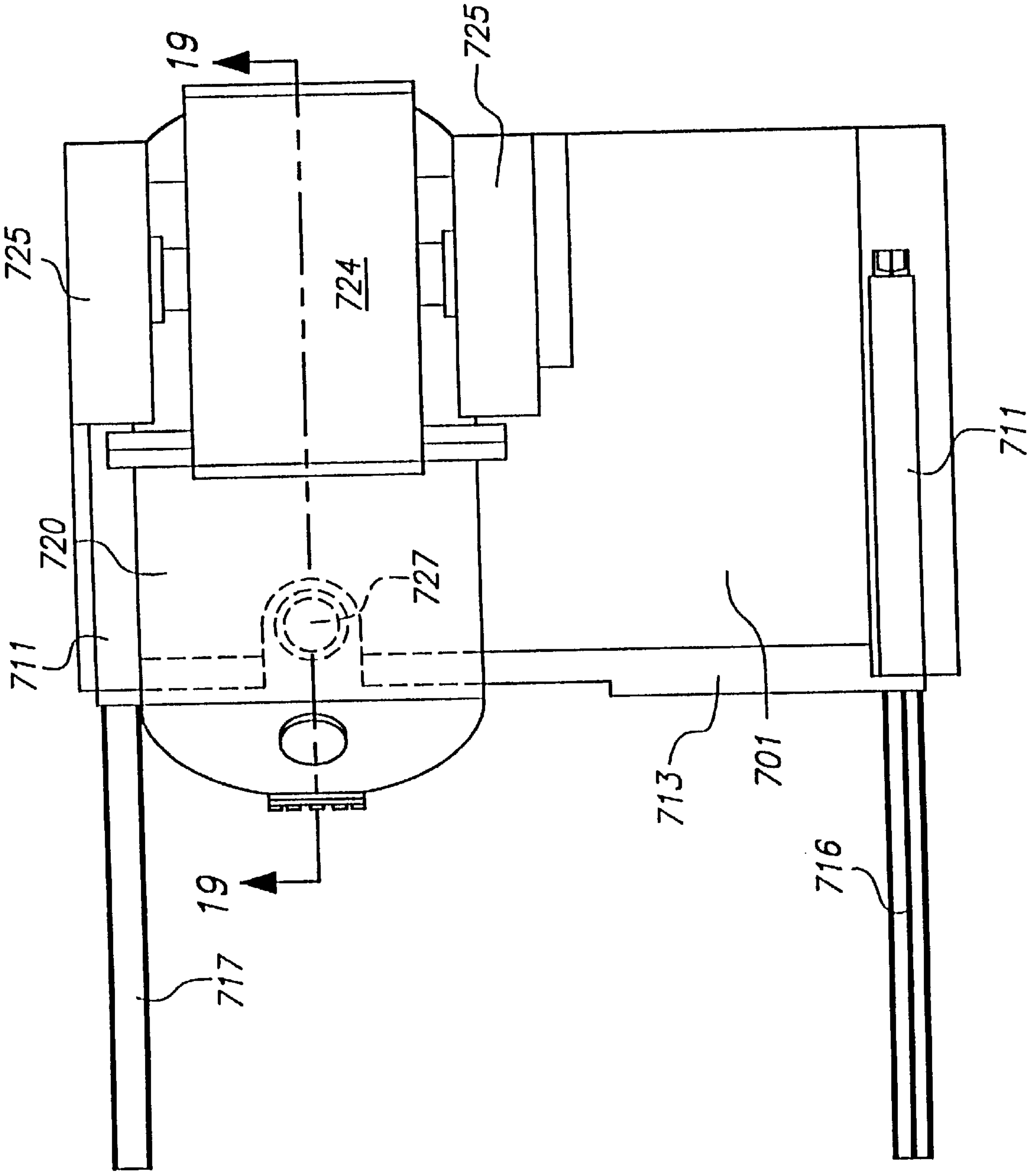
FIG. 20 is a top view of the FIG. 15 embodiment.

FIG. 14 illustrates diagrammatically a protection device for an apparatus for irradiating a substrate to protect against damage to the vacuum system and accelerator tube due to vacuum failure. Such failure may occur because of failure of the window at the first end of the vacuum chamber, leading to an implosion, and causing debris to enter the vacuum chamber at considerable velocity. The vacuum chamber 645 of the apparatus for irradiating a substrate comprises a drift tube 650 and 651, which connects the particle accelerator 655 to the vacuum chamber, the drift tube also comprising vacuum connection means 650 and 652 for connecting the vacuum chamber 645 to vacuum pump means 654. Between the connection means 650 and the first end 660 of the vacuum chamber, the drift tube portion 651 forms a diversion chamber 651, having an exit 656 and entrance 657, the exit facing the target or first end 660 of the vacuum chamber and being at a finite angle less than 180° to the longitudinal axis of the drift tube segment 650 at the entrance 657 through which the particle beam 658 enters the diversion chamber 651. The diversion chamber 651 further comprises means 662 for redirecting and scanning the particle beam, comprising a 90° deflection and scanning magnet 659, so that it is directed toward the exit 656. The segment of drift tube 651 between the scanning means 662 and the target end 661 of the housing is widened, thereby accommodating any trajectory variance due to scanning of the particle beam. The means 662 for redirecting and scanning the particle beam comprises a 90° deflection and scan magnet energized by two coils, one for providing the 90° deflection and the other for scanning the particle beam along the transmission window 665 at the target end 660 of the vacuum chamber. The diversion chamber comprises a blind tube or recess 653 which projects beyond the entrance 657 of the diversion chamber such that inertial forces acting on any implosion debris, entering the diversion chamber through failure, for example, of the transmission window, will cause the debris to enter the blind tube or recess 653. Further protection for the vacuum system and accelerator tube is provided by a diaphragm 663 having a narrow restriction orifice 664 at the center thereof to permit passage of the particle beam therethrough, but impede entry of implosion debris from the diversion chamber into the rest of the vacuum system and the accelerator tube.

FIGS. 15–22 illustrate the shielding system of the invention. The shielded vault comprises an enclosure 700 open at one end, the walls of which in a preferred embodiment comprise a hollow steel ceiling 701 and walls 702, which are filled in known fashion with a radiation absorbing material, for example, water or lead. A door frame structure 710 comprises a hollow steel door 713, also filled with a radiation absorbing material, removably secured to the open end of the enclosure. The door frame structure 710 includes vertical and horizontal support girders 711 which are mounted via guide wheels 714 on a base guide structure 715, which is attached to the shield vault enclosure and comprises guide rails 716 and 717.

One or more components of the apparatus for irradiating a substrate are secured to the door frame structure. In particular, a power supply enclosure 720 comprising the voltage multiplier, which is preferably of the invention, and preferably comprising the auxiliary power supply of the invention, is secured to the door frame structure 710 by means of supports 703 and 704. The enclosure is in the form of two dome shaped members secured together by means of flanges 718. On top of the power supply enclosure 720 and secured thereto is a transformer enclosure 724, preferably comprising inductors of the invention. The transformer enclosure has appended thereto on either side an RF drive enclosure 725 secured thereto via flanges 726, each RF drive enclosure preferably comprising power transfer apparatus of the invention. Preferably, the power supply enclosure 720 and the transformer enclosure 724 are each capable of withstanding internal gas pressure and contain a dielectric gas, for example sulfur hexafluoride, under pressure.

Within a high pressure tube 727 connecting the power supply enclosure 720 to the accelerator enclosure 728 (see FIG. 16) are a high voltage electrical power connection and auxiliary power supply connections (neither shown) to a vacuum chamber partly within the accelerator enclosure 728. That part of the vacuum chamber within the accelerator enclosure 728 comprises a particle accelerator tube, which is secured to an upper part of the drift tube comprising a tube 731 and vacuum connection means 732 which is secured to a vacuum pump means 733. Also shown is a sump 755 of a liquid processing unit which, in a preferred embodiment of this apparatus, is secured to the window assembly at the first end of the vacuum chamber. Preferably, one or more of the accelerator enclosure, the first part of the drift tube, the vacuum pump means, the diversion chamber, the window assembly (not shown in this view) and the liquid processing unit is secured to the door frame structure. Yet more preferably, each one of the components of the apparatus is secured directly or indirectly to the door frame structure. Most preferably, the accelerator enclosure, the first part of the drift tube, the vacuum pump means, the diversion chamber, the window assembly, the liquid processing unit, and the door, all travel together as a unit on the door frame structure.

Figure 21:
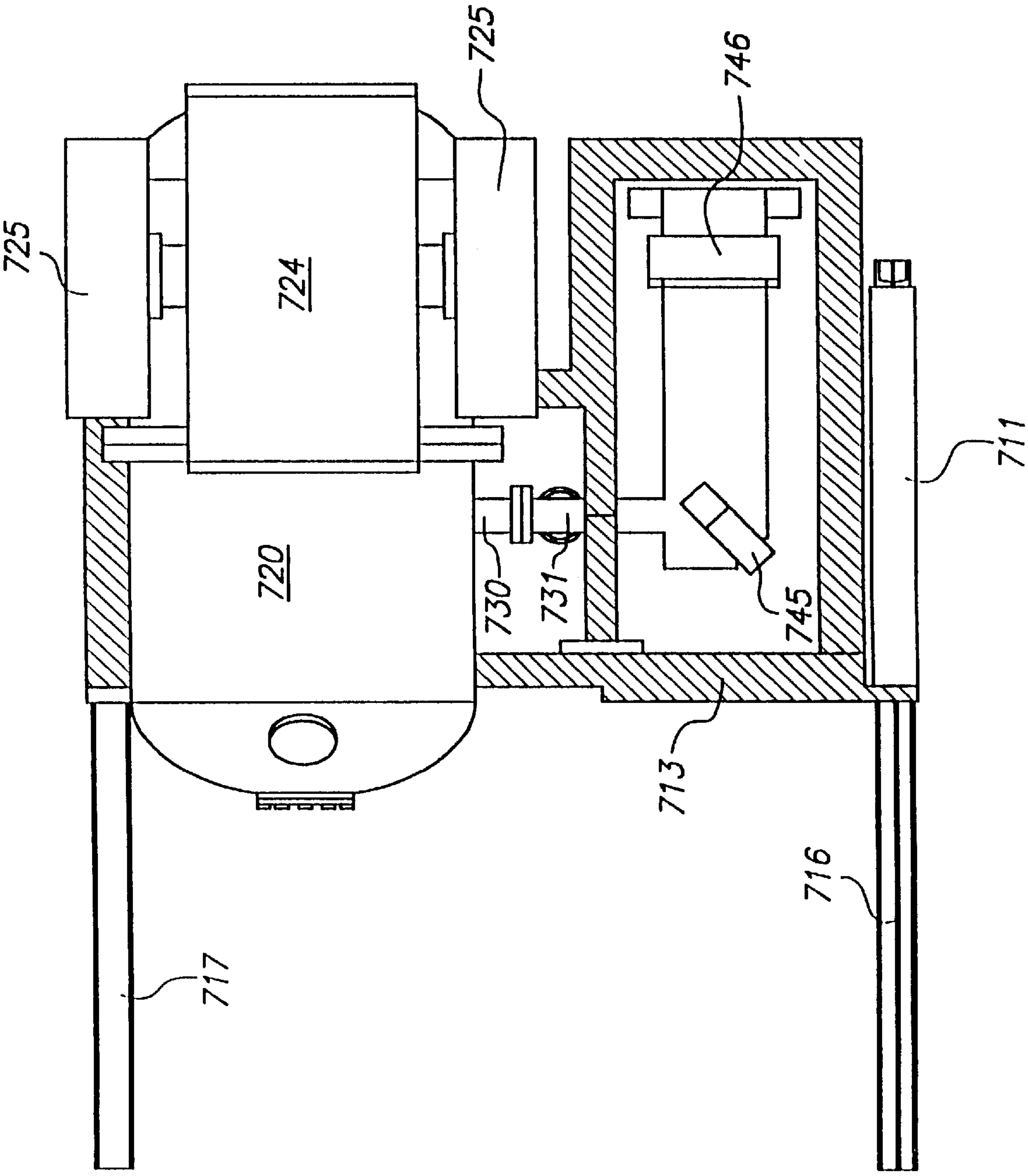
FIG. 21 illustrates the FIG. 20 embodiment with the top shield wall removed to better show the component arrangement therewithin.

FIG. 21 shows a view of interior components of the self-shielded apparatus for irradiating a substrate of the invention as seen from above. In this view the door 713 of the door frame structure can be seen as can the 90° redirecting and scanning magnet structure 745 and the window assembly 746 comprising the target end of the vacuum housing.

Figure 22:
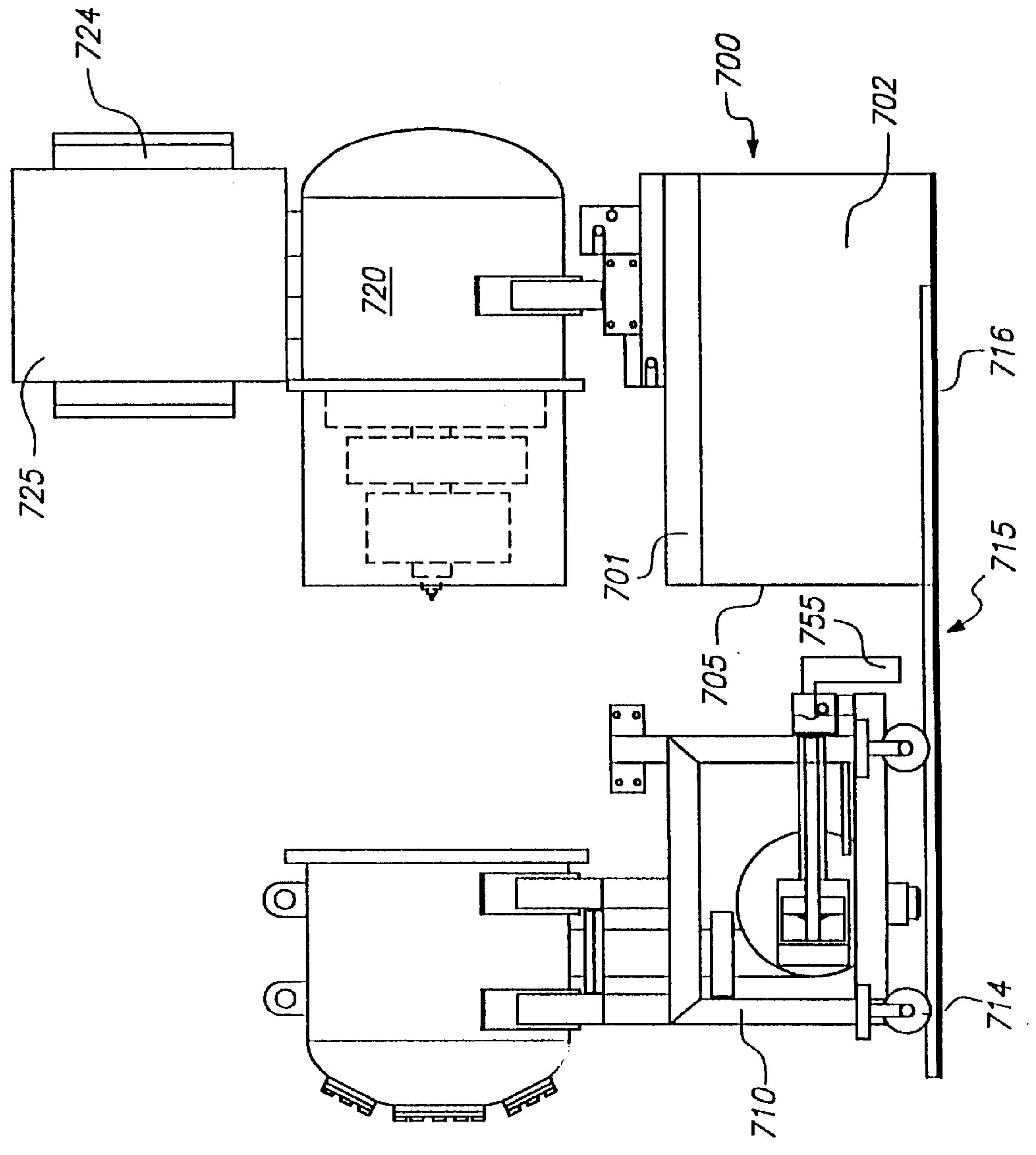
FIG. 22 is a view similar to FIG. 17 but showing the shield door and the apparatus components which are supported thereon in the opened position.

FIG. 22 shows a side diagrammatic view of the self-shielded apparatus for irradiating a substrate of the invention with the vault opened to provide access to the accelerator apparatus. As before, the shielded vault comprises an enclosure 700 having walls 702 and a ceiling 701 and being open at one end 705. A base guide structure 715 having guide rails (716 being shown in this figure) mounted thereon is secured to the vault. The door frame structure 710 is slidably mounted via guide wheels 714 which run on the guide rails.

In a particularly preferred embodiment, the apparatus for irradiating a substrate of the invention also comprises a window assembly and liquid processing unit (each of which is disclosed in copending U.S. patent application Ser. No. 07/950,530). It can be used in oil fields for crude oil viscosity reduction and local cracking to produce refined products for field use. It may be used to lower the hydraulic horsepower required for pumping through pipelines. It may be taken to and advantageously employed to reduce or eliminate toxic contaminants in waste streams or in potable water supplies.

Preferably, in all embodiments of the apparatus for irradiating substrates of the invention, the transmission window, at the first end of the vacuum chamber, is generally rectangular in shape when viewed in the direction of the particle beam and convex towards the vacuum chamber when viewed along the longitudinal axis of the window, with a radius of curvature which, when measured in the absence of a pressure differential across the window is (a) at most twice the width of the rectangle, and (b) does not deviate from the average radius of curvature by more than 5%, as disclosed in U.S. patent applications Ser. Nos. 07/950,530 and 08/198,163. Preferably, in all embodiments of the apparatus for irradiating a substrate of the invention, the particle accelerator comprises an all inorganic ion beam focusing and directing structure, for example, one formed from metal and ceramic components. Thus, the particle beam focusing and directing structure is preferably an ion acceleration tube assembly comprising tube segments formed of ceramic and metal, for example, alumina ceramic and titanium components conventionally bonded together by heat, pressure and suitable fluxes, and containing internal electrodes. These segments may be bolted together using metal gasket seals (for example, gold, aluminum, copper, or tin wire seals) between the component segments. A particular advantage of such structures is that, should a catastrophic condition occur, such as a beam transmission window implosion, the tube assembly can be disassembled quickly and the components cleaned and vacuum baked at a high temperature, that is up to 200° C., without harm to the components. Preferably, the internal electrodes are demountable to facilitate cleaning of the components and electrodes. An especially preferred acceleration tube assembly is one intended for ion acceleration and is manufactured by National Electrostatics Corporation.

Having thus described these embodiments of the present invention, it will now be appreciated that the objects of the invention have been fully achieved, and it will be understood by those skilled in the art that many further changes in construction and widely differing embodiments and applications will suggest themselves without departing from the spirit and scope of the invention, as particularly defined by the following claims.

What is claimed is:

1. Apparatus for irradiating a substrate comprising:

(i) a vacuum chamber including a transmission window which is located at a first end of said vacuum chamber;

(ii) a particle beam generator within said vacuum chamber; and (iii) a particle beam accelerator, within said vacuum chamber, which accelerates and directs particles from said generator towards and through said transmission window, said apparatus comprising an inductor having:

(i) a pair of high voltage terminals, and (ii) a first inductive component having a first inductance and a second inductive component having a second inductance, said inductive components being spaced close together and substantially parallel to one another and each comprising a plurality of turns, said turns of said second inductive component being wound in an opposite clockwise sense to said turns in said first inductive component, and said turns of said first and second inductive components being electrically connected in series between said high voltage terminals to form said inductor, which has a total inductance and is so configured that said high voltage terminals are spatially remote from each other and said total inductance is greater than either said first inductance or said second inductance.

2. Apparatus according to claim 1, wherein:

(i) the first inductive component has a predetermined length and comprises a predetermined number of conductor turns divided into a plurality of first sequences each comprising one or more conductor turns each turn having a predetermined shape; and (ii) the second inductive component, adjacent to and substantially parallel to the first inductive component, has a predetermined length and number of turns which is substantially similar to that of the first inductive component, and comprises a predetermined number of conductor turns divided into a plurality of second sequences each comprising one or more conductor turns substantially identical in shape to those of the first inductive component but opposite in winding sense;

each one of the first sequences being series connected end to end with at least one second sequence and each one of the second sequences being series connected end to end with at least one first sequence to form an electrically conductive path which alternates between the first and second inductive components;

such that the inductive contribution of a sequence of conductor turns is 25% or less of the total inductance of the inductor.

3. Apparatus according to claim 2 wherein at least one of said conductor turns comprises Litz wire.

4. Apparatus according to claim 2 wherein the inductive contribution of a sequence of conductor turns is 5% or less of the total inductance of the inductor.

5. Apparatus according to claim 2, wherein each one of the first and second sequences of conductor turns comprises less than 11 turns.

6. Apparatus according to claim 2, wherein each one of the first and second sequences of conductor turns comprises two turns.

7. Apparatus according to claim 2, wherein the total number of turns in the inductor is even.

8. Apparatus according to claim 7, wherein the total number of turns in the first inductive component is equal to the total number of turns in the second inductive component.

9. Apparatus according to claim 2, wherein each conductor turn of the first and of the second inductive component is D shaped such that each inductive component is in the general form of a cylinder halved longitudinally along a diameter and the two inductor components are positioned face to face along the diametrical faces of the half cylinders.

10. Apparatus according to claim 9, wherein the segments of a turn that transition from one inductive component to the other are common to both inductive components.

11. Apparatus according to claim 1 wherein each of first and second inductive components is disposed substantially along a linearly elongated axis of said component.

12. Apparatus according to claim 2, which comprises a plurality of flat conductor turns secured together to be electrically in parallel at one or more positions along the turns and separated by gaseous, liquid, or solid dielectric material at all other positions along the turns.

13. Apparatus according to claim 2, and wherein each of first and second inductive components has a first and a second end, and has a first set of corresponding turns at said one end, a second set of corresponding turns adjacent to but separated from said end by said first set, and successive sets of corresponding turns still further from but similarly separated from said end by sets of corresponding turns nearer said end, whereby the turns of each set form an angle with one another, which increases from an acute angle for the set of corresponding turns at said end to an increasingly more obtuse angle as the distance of a set of corresponding turns from said end increases to a maximum of 180°.

14. Apparatus according to claim 2, and wherein each of first and second inductive components has a first and a second end, and has a first set of corresponding turns at said first and at said second end, a second set of corresponding turns adjacent to but separated from said first and said second end by said first set, and successive sets of corresponding turns still further from but similarly separated from said first and said second end by sets of corresponding turns nearer each one of said ends, whereby the turns of each set form an angle with one another, which increases from an acute angle for the set of corresponding turns at said ends to an increasingly more obtuse angle as the distance of a set of corresponding turns from said ends increases, to a maximum of 180°.

15. Apparatus according to claim 14 wherein the turns of each said set at said inductor ends comprise at most two turns formed of Litz wire.

* * * * *

UNITED STATES PATENT AND TRADEMARK OFFICE

CERTIFICATE OF CORRECTION

PATENT NO. : 5,883,392
DATED : March 16, 1999
INVENTOR(S) : Schuetz

It is certified that error appears in the above-identified patent and that said Letters Patent is hereby corrected as shown below:

Column 2, line 66: replace"RT" by --RF--
Column 12, line 16: replace "clerical" by --electrical--
Column 13, line 23: replace "die" by --the--
Column 20, line 45: replace "anticloclkwise" by --anticlockwise--
Column 26, line 28, replace "night" by --might--

Signed and Sealed this

Fifteenth Day of August, 2000

Attest:

Q. TODD DICKINSON

Attesting Officer

*Director of Patents and Trademarks*